US008002847B2

(12) United States Patent
Audousset et al.

(10) Patent No.: US 8,002,847 B2
(45) Date of Patent: Aug. 23, 2011

(54) COMPOSITION FOR OXIDATION DYEING KERATIN FIBRES COMPRISING A CATIONIC CELLULOSE ETHER, A WEAKLY OXYETHYLENATED SORBITAN FATTY ACID ESTER AND OXIDATION DYES

(75) Inventors: Marie-Pascale Audousset, Asnieres (FR); Isabelle Schlosser, Paris (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 12/671,448

(22) PCT Filed: Jul. 21, 2008

(86) PCT No.: PCT/EP2008/059533
§ 371 (c)(1), (2), (4) Date: Jul. 12, 2010

(87) PCT Pub. No.: WO2009/016061
PCT Pub. Date: Feb. 5, 2009

(65) Prior Publication Data
US 2010/0275388 A1  Nov. 4, 2010

Related U.S. Application Data

(60) Provisional application No. 60/935,742, filed on Aug. 29, 2007.

(30) Foreign Application Priority Data

Jul. 31, 2007 (FR) .................................... 07 56858

(51) Int. Cl.
*A61Q 5/10* (2006.01)
(52) U.S. Cl. ............. 8/405; 8/406; 8/408; 8/435; 8/552; 8/561; 8/562
(58) Field of Classification Search .............. 8/405, 406, 8/408, 435, 552, 561, 562
See application file for complete search history.

(56) References Cited

U.S. PATENT DOCUMENTS

| 7,115,147 B2 | 10/2006 | Desenne et al. | |
| 2005/0229330 A1* | 10/2005 | Cottard et al. | 8/405 |
| 2007/0079451 A1 | 4/2007 | Audousset et al. | |
| 2007/0151044 A1* | 7/2007 | Cassier et al. | 8/405 |

FOREIGN PATENT DOCUMENTS

| EP | 1 321 135 A2 | 6/2003 |
| FR | 2 889 660 A1 | 2/2007 |
| WO | WO 2006/088973 A1 | 8/2006 |
| WO | WO 2006/099163 A1 | 9/2006 |

OTHER PUBLICATIONS

STIC Search Report dated Sep. 30, 2010.*
T.V. Drovetskaya et al., "Effects of low-level hydrophobic substitution on conditioning properties of cationic cellulosic polymers in shampoo systems," Journal of Cosmetic Science, vol. 55, No. Suppl., pp. 195-205 (2004).
French Search Report for FR 0756858, dated Mar. 28, 2008.
International Search Report for PCT/EP2008/059533, dated May 7, 2009.

* cited by examiner

*Primary Examiner* — Eisa B Elhilo
(74) *Attorney, Agent, or Firm* — Finnegan, Henderson, Farabow, Garrett & Dunner LLP

(57) ABSTRACT

The present invention relates to a dye composition comprising, in a medium suitable for dyeing: A) one or more particular cationic cellulose ether(s), B) one or more weakly oxyethylenated sorbitan fatty acid ester(s), and C) one or more oxidation dye(s). The present invention also relates to a process for dyeing keratin fibers using such a composition, and also to the use of this composition for dyeing keratin fibers.

43 Claims, No Drawings

COMPOSITION FOR OXIDATION DYEING KERATIN FIBRES COMPRISING A CATIONIC CELLULOSE ETHER, A WEAKLY OXYETHYLENATED SORBITAN FATTY ACID ESTER AND OXIDATION DYES

CROSS REFERENCE TO RELATED APPLICATIONS

This application is a national phase application based on PCT/EP2008/059533, filed Jul. 21, 2008, which claims the priority of French Patent Application No. 0756858, filed Jul. 31, 2007; and claims the benefit of U.S. Provisional Application No. 60/935,742, filed Aug. 29, 2007, the contents of all of which are incorporated herein by reference.

The present invention relates to a composition for oxidation dyeing keratin fibres, and in particular human keratin fibres such as the hair, comprising one or more cationic cellulose ether(s), one or more weakly oxyethylenated sorbitan fatty acid ester(s), and one or more oxidation dye(s).

The invention also relates to the use of this composition for dyeing keratin fibres and also to the dyeing process using this composition.

It is known practice to dye keratin fibres, and in particular human hair, with dye compositions containing oxidation dye precursors, generally known as oxidation bases, such as ortho- or para-phenylenediamines, ortho- or para-aminophenols and heterocyclic compounds. These oxidation bases are colourless or weakly coloured compounds which, when combined with oxidizing products, can produce coloured compounds via a process of oxidative condensation.

It is also known that the shades obtained with these oxidation bases can be varied by combining them with couplers or colouration modifiers, the latter being chosen in particular from aromatic meta-diamines, meta-aminophenols, meta-diphenols and certain heterocyclic compounds such as indole compounds.

The variety of molecules used as regards the oxidation bases and couplers allows a wide range of colours to be obtained.

The "permanent" colouration obtained by virtue of these oxidation dyes should, moreover, meet a certain number of requirements. Thus, it should have no toxicological drawbacks, it should allow shades to be obtained in the desired strength, and it should show good fastness with respect to external agents such as light, bad weather, washing, permanent-waving, perspiration and rubbing.

The dyes should also allow grey hair to be covered and, finally, should be as nonselective as possible, i.e. they should make it possible to produce the smallest possible differences in colouration along the same keratin fibre, which is generally differently sensitized (i.e. damaged) between its tip and its root.

The use of weakly oxyethylenated sorbitan fatty acid esters in oxidation dyeing compositions for keratin fibres is known in particular, through Patent Application DE-A-19923438, to reduce staining of the scalp during dyeing, or through Patent Applications FR-A-2 889 660 and FR-A-2 889 661, to limit the discomfort that may be felt by the user during dyeing.

The use of cationic cellulose ethers in oxidation dyeing compositions for keratin fibres is known in particular through Patent Application WO 2006/099163.

The objective of the present invention is to obtain stable hair dyeing compositions, in particular in the form of creams, which are easy to prepare and to apply, which have good rheological qualities and which produce relatively nonselective colourations that withstand the various attacks that keratin fibres may be subjected to.

Surprisingly and advantageously, the Applicant has discovered that the use, in combination, of one or more particular cationic cellulose ether(s), of one or more weakly oxyethylenated sorbitan fatty acid ester(s) and of one or more dye(s) chosen from oxidation dyes makes it possible to obtain hair dyeing compositions of very good quality with improved properties.

The dye compositions according to the invention have in particular the following properties:
 these dye compositions may comprise dyes in the form of salts in high concentrations without showing stability problems,
 it is possible to obtain compositions with a viscosity corresponding to a cream, which are stable over time,
 these compositions stand out by virtue of the fact that they can be easily mixed with the oxidizing composition,
 these compositions stand out by virtue of the rheological qualities of the creams obtained (good viscosity of cream as mixture),
 ease of application of the compositions after mixing with the oxidizing composition at the time the dyeing is carried out (qualities of use on the head).

In addition, the compositions according to the invention make it possible to obtain compositions capable of producing varied, chromatic, powerful, aesthetic and relatively nonselective shades which are uniform over the entire head of hair and which are highly resistant to the various attacks to which the hair may be subjected.

These compositions are also nonaggressive for the scalp when applied.

A subject of the present invention is a dye composition for keratin fibres, and in particular for human keratin fibres such as the hair, comprising, in a medium suitable for dyeing, one or more particular cationic cellulose ether(s) described below, one or more weakly oxyethylenated sorbitan fatty acid ester(s), and one or more oxidation dye(s).

Another subject of the present invention comprises a process for dyeing keratin fibres, in which the cosmetic composition according to the invention is used.

A third subject of the invention relates to the use of this cosmetic composition for dyeing keratin fibres, and in particular human keratin fibres such as the hair.

Other features, aspects, subjects and advantages of the present invention will emerge more clearly on reading the description and the examples which follow.

The dye composition for keratin fibres, according to the invention, comprises, in a medium suitable for dyeing:
A) one or more cationic cellulose ether(s) comprising from 4000 to 10 000 anhydroglucose units, said anhydroglucose units being substituted with at least:
 (i) one substituent of formula $[R_4R_5R_6R_9N^+](X_2^-)$, in which:
 $R_4$ and $R_5$ represent, independently of one another, a methyl or ethyl group,
 $R_6$ represents a linear or branched $C_8$-$C_{24}$ alkyl group or an aralkyl group in which the linear or branched alkyl part is $C_8$-$C_{24}$,
 $R_9$ represents a divalent group which allows the attachment to the anhydroglucose group and which is chosen from —(B)$_q$—CH$_2$—CHOH—CH$_2$— and —CH$_2$CH$_2$—,
 q denoting 0 or 1,
 B denoting a divalent group —(CH$_2$CH$_2$O)$_{n'}$—,
 n' being an integer ranging from 1 to 100,
 $X_2^-$ represents an anion; and (ii) one substituent of formula [R$_1$R$_2$R$_3$R$_8$N$^+$](X$_1^-$), in which:

R$_1$, R$_2$ and R$_3$ represent, independently of one another, a methyl or ethyl group, R$_8$ represents a divalent group which allows the attachment to the anhydroglucose group and which is chosen from -(A)$_p$-CH$_2$—CHOH—CH$_2$— and —CH$_2$CH$_2$—, p denoting 0 or 1, A denoting a divalent group —(CH$_2$CH$_2$O)$_n$—, n being an integer ranging from 1 to 100, X$_1^-$ represents an anion;

B) one or more weakly oxyethylenated sorbitan fatty acid ester(s); and

C) one or more oxidation dye(s).

Preferably, the substituent (i) of formula [R$_4$R$_5$R$_6$R$_9$N$^+$](X$_2^-$) is present at an average of from 0.0003 to 0.08 mol, per mole of anhydroglucose units.

The cationic cellulose ethers that can be used in the compositions according to the invention are preferably hydroxyethylcelluloses or hydroxypropylcelluloses.

The cationic cellulose ethers that can be used in the compositions according to the invention preferably comprise more than 4500, advantageously more than 5000, and more preferably more than 6000 anhydroglucose units.

Preferably, the cationic cellulose ethers that can be used in the compositions according to the invention preferably comprise up to 9000, and preferably up to 8000 anhydroglucose units.

These cationic cellulose ethers and the process for the preparation thereof are described in application WO 2005/000903.

According to a preferred variant, the cationic cellulose ethers that can be used in the compositions according to the invention are formed from at least one unit (IV) and at least one of the following units (I), (II) and (III):

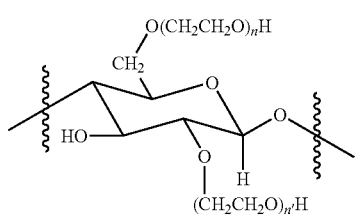
(I)

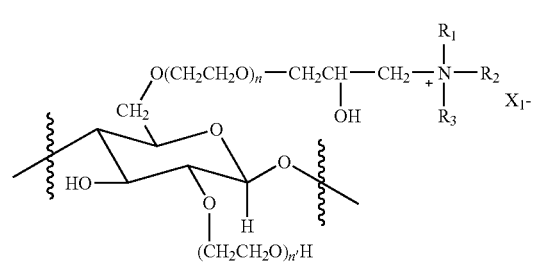
(II)

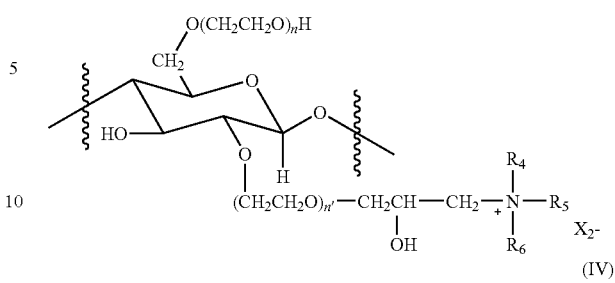
(III)

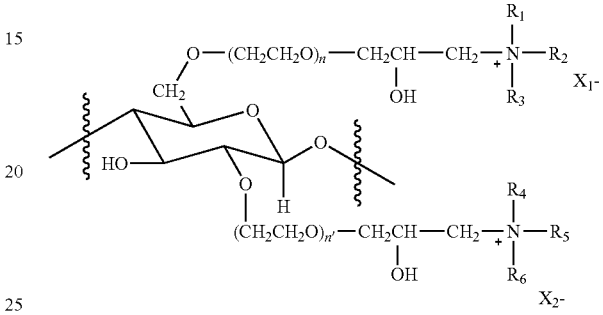
(IV)

with the proviso that:

the total number of units (I)+(II)+(III)+(IV) is between 4000 and 10 000;

the [(III)+(IV)]/[(I)+(II)+(III)+(IV)] ratio ranges from 0.0003 to 0.8;

the [(II)+(IV)]/[(I)+(II)+(III)+(IV)] ratio ranges from 0.02 to 0.9;

the integers n and n', independently of one another, range from 0 to 5;

R$_1$, R$_2$, R$_3$, R$_4$ and R$_5$ represent, independently of one another, a methyl or ethyl group;

R$_6$ represents a linear or branched C$_8$-C$_{24}$, preferably C$_{10}$-C$_{24}$, more preferably C$_{12}$-C$_{24}$ and better still C$_{12}$-C$_{15}$, alkyl group or an aralkyl group in which the linear or branched alkyl part is C$_8$-C$_{24}$;

X$_1^-$ and X$_2^-$ represent anions preferably chosen, independently of one another, from phosphate, nitrate, sulphate and halide (Cl$^-$, Br$^-$, F$^-$, I$^-$) ions.

According to a particular variant, the cationic cellulose ethers that can be used in the compositions according to the invention are formed from at least one unit (IV) and at least one of the units (I), (II) or (III) above, in which R$_6$ is a linear dodecyl group.

Among the cationic cellulose ethers that can be used in the compositions of the invention, mention may be made of the polymers of Softcat SL-5, SL-30, SL-60 and SL-100 type (INCI: Polyquaternium-67) sold by the company Amerchol. The cationic cellulose ethers that are particularly preferred are the polymers of SL-60 and SL-100 type.

The composition according to the invention may comprise one or more cationic cellulose ether(s) as defined above.

The concentration of cationic cellulose ether(s) of the compositions according to the invention preferably ranges from 0.01% to 10% by weight, in particular from 0.05% to 3% by weight, and more preferably from 0.1% to 1% by weight, relative to the total weight of the composition.

The weakly oxyethylenated sorbitan fatty acid ester or ester(s) that can be used in the compositions of the invention generally have fewer than 10 ethylene oxide units, preferably from 2 to 9 ethylene oxide units, more preferably from 4 to 5 ethylene oxide units, and better still 4 ethylene oxide units.

By way of sorbitan fatty acid esters that can be used, mention may in particular be made of oxyethylenated derivatives of sorbitan $C_8$-$C_{30}$ fatty acid monoesters and polyesters having fewer than 10 ethylene oxide units. Oxyethylenated derivatives of sorbitan $C_{12-24}$ fatty acid monoesters and polyesters having from 4 to 5 ethylene oxide units are preferably used.

Such compounds are also known as polysorbates. They are, inter alia, sold under the name Tween® by the company Uniqema. Mention is made, for example, of: oxyethylenated sorbitan monolaurate comprising 4 mol of ethylene oxide, sold under the name Tween® 21, oxyethylenated sorbitan monostearate comprising 4 mol of ethylene oxide, sold under the name Tween® 61, and oxyethylenated sorbitan monooleate comprising 5 mol of ethylene oxide, sold under the name Tween® 81.

In the present application, and in a manner well known per se, the term "compound comprising X EO" denotes an oxyethylenated compound comprising X units of ethylene oxide per molecule or comprising on average X moles of ethylene oxide per mole of ester.

Preferably, the fatty acid of the oxyethylenated sorbitan ester is a linear fatty acid, and in particular a saturated fatty acid.

Particularly preferably, the preferred sorbitan ester is oxyethylenated sorbitan monolaurate comprising 4 EO.

The concentration of weakly oxyethylenated sorbitan fatty acid ester(s) of the compositions according to the present application preferably ranges from 1% to 20% by weight, and more preferably from 3% to 10% by weight, relative to the total weight of the composition.

The oxidation dye(s) that can be used according to the invention is (are) preferably chosen from benzene, heterocyclic and naphthalene oxidation dyes.

The oxidation dye(s) that can be used in the compositions of the invention may be in particular chosen from cationic or noncationic benzene bases, heterocyclic bases, benzene couplers, heterocyclic couplers and naphthalene couplers.

Preferably, the compositions according to the invention contain one or more oxidation base(s).

The benzene oxidation base(s) may be cationic or noncationic.

By way of noncationic benzene oxidation bases that can be used, mention may be made of para-phenylenediamines, bisphenylalkylenediamines, para-aminophenols and ortho-aminophenols, and addition salts thereof.

Among para-phenylenediamines of this type, mention may be made, by way of example, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl,β-hydroxyethyl)-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and addition salts thereof.

Among the para-phenylenediamines mentioned above, para-phenylenediamine, para-toluoylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and addition salts thereof, are particularly preferred.

Among the noncationic bisphenylalkylenediamines, mention may, by way of example, be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis-(4-methylaminophenyl)-tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and addition salts thereof.

Among the noncationic para-aminophenols, mention may, by way of example, be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and addition salts thereof.

Among the noncationic ortho-aminophenols, mention may, by way of example, be made of 2-aminophenol, 2-amino-5-methylphenol, 2-amino-6-methylphenol, 5-acetamido-2-aminophenol, and addition salts thereof.

By way of cationic benzene oxidation bases that can be used in the compositions according to the invention, mention may be made of para-phenylenediamines as in particular described in Patent Applications FR-A-2 766 177 and FR-A-2 766 178, para-aminophenols as described, for example, in Patent Applications FR-A-2 766 177 and FR-A-2 766 178, ortho-phenylenediamines as described, for example, in Patent Applications FR-A-2 782 718, FR-A-2 782 716 and FR-A-2 782 719, ortho-aminophenols or double cationic bases such as derivatives of bis(aminophenyl)alkylenediamine type, described in Patent Application FR-A-2 766 179, bearing at least one quaternary nitrogen atom.

Preferably, the cationic benzene oxidation bases that can be used in the composition according to the invention are cationic para-phenylenediamines.

Advantageously, a variant consists in using cationic oxidation bases of para-phenylenediamine structure, at least one of the amine functions of which is a tertiary amine, bearing a pyrrolidine nucleus, the molecule having at least one quaternized nitrogen atom. Such bases are, for example, described in document EP-A-1 348 695.

According to a variant, the dye composition according to the invention comprises at least one cationic para-phenylenediamine chosen from the following compounds:

| Formula | Nomenclature |
|---|---|
| (structure) | [1-(4-aminophenyl)-pyrrolidin-3-yl]-trimethylammonium; chloride (1) |
| (structure) | [1-(4-aminophenyl)-pyrrolidin-3-yl]-dimethyltetradecyl-ammonium; bromide (2) |
| (structure) | 3-[1-(4-aminophenyl)-pyrrolidin-3-yl]-1-methyl-3H-imidazol-1-ium; chloride (3) |
| (structure) | [1-(4-aminophenyl)-pyrrolidin-3-yl]-(2-hydroxyethyl)dimethyl-ammonium; chloride (4) |
| (structure) | [1-(4-aminophenyl)-pyrrolidin-3-yl]-dimethyl-(3-trimethyl-silanylpropyl)-ammonium; chloride (5) |
| (structure) | [1-(4-aminophenyl)-pyrrolidin-3-yl]-(3-trimethylammonium-hexyl)dimethyl-ammonium; dichloride (6) |
| (structure) | {2-[1-(4-aminophenyl)-pyrrolidin-3-yloxy]-ethyl}trimethyl-ammonium; chloride (7) |
| (structure) | 1-{2-[1-(4-amino-phenyl)pyrrolidin-3-yl-oxy]ethyl}-1-methy-pyrrolidinium; chloride (8) |
| (structure) | 3-{3-[1-(4-amino-phenyl)pyrrolidin-3-yl-oxy]-propyl}-1-methyl-3H-imidazol-1-ium; chloride (9) |

| Formula | Nomenclature |
|---|---|
| | 1-{2-[1-(4-amino-phenyl)pyrrolidin-3-yl-oxy]ethyl}-1-methy-piperidinium; chloride (10) |
| | 3-{3-[1-(5-trimethyl-silanylethyl-4-amino-3-trimethylsilanylethyl-phenyl)pyrrolidin-3-yl-oxy]propyl}-1-methyl-3H-imidazol-1-ium; chloride (11) |
| | [1-(4-amino-3-methyl-phenyl)pyrrolidin-3-yl]trimethylammonium; chloride (12) |
| | [1-(4-amino-3-methyl-phenyl)pyrrolidin-3-yl]-dimethyltetradecyl-ammonium; chloride (13) |
| | 3-[1-(4-amino-3-methylphenyl)-pyrrolidin-3-yl]-1-methyl-3H-imidazol-1-ium; chloride (14) |
| | [1-(4-amino-3-methylphenyl)-pyrrolidin-3-yl]-(2-hydroxyethyl)dimethyl-ammonium; chloride (15) |
| | [1-(4-amino-3-methylphenyl)-pyrrolidin-3-yl]dimethyl-(3-trimethylsilanylpropyl ammonium; chloride (16) |
| | [1-(4-amino-3-methylphenyl)-pyrrolidin-3-yl]-(3-trimethylammonium-hexyl)dimethyl-ammonium; dichloride (17) |
| | {2-[1-(4-amino-3-methylphenyl)-pyrrolidin-3-yloxy]-etyl}trimethyl-ammonium; chloride (18) |
| | 1-{2-[1-(4-amino-3-methylphneyl)-pyrrolidin-3-yloxy]-ethyl}-1-methyl-pyrrolidinium; chloride (19) |

| Formula | Nomenclature |
|---|---|
| 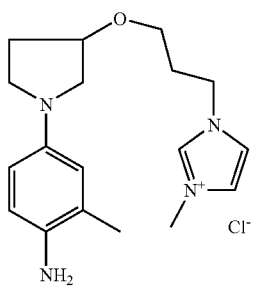 | 3-{3-[1-(4-amino-3-methylphenyl)-pyrrolidin-3-yloxy]propyl}-1-methyl-3H-imidazol-1-ium; chloride (20) |
| 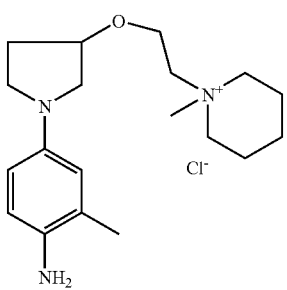 | 1-{2-[1-(4-amino-3-methylphenyl)-pyrrolidin-3-yloxy]ethyl-1-methylpiperidinium; chloride (21) |
| 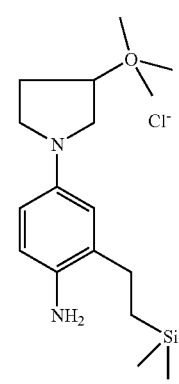 | [1-(4-amino-3-trimethylsilanylethylphenyl)pyrrolidin-3-yl]-trimethylammonium; chloride (22) |
| 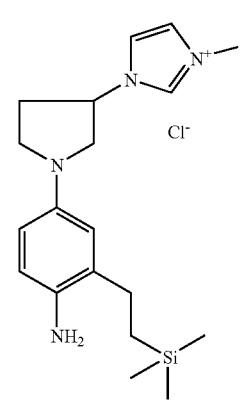 | 3-[1-(4-amino-3-trimethylsilanylethylphenyl)pyrrolidin-3-yl]-1-methyl-3H-imidazol-1-ium; chloride (23) |
| 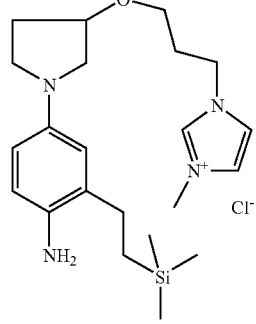 | 3-{3-[1-(4-amino-3-trimethylsilanylethylphenyl)pyrrolidin-3-yloxy]propyl}-1-methyl-3H-imidazol-1-ium; chloride (24) |
| 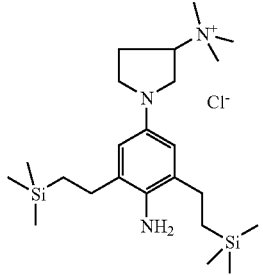 | [1-(5-trimethylsilanyl-ethyl-4-amino-3-trimethylsilanylethylphenyl)pyrrolidin-3-yl]trimethylammonium; chloride (25) |
| 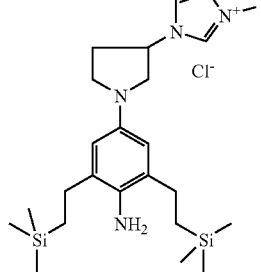 | 3-[1-(5-trimethyl-silanylethyl-4-amino-3-trimethyl-silanylethylphenyl)-pyrrolidin-3-yl]-1-methyl-3H-imidazol-1-ium; chloride (26) |
| 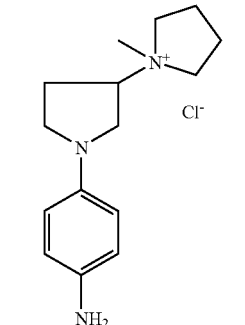 | 1'-(4-aminophenyl)-1-methyl-[1,3*]-bipyrrolidinyl-1-ium; chloride (27) |
| 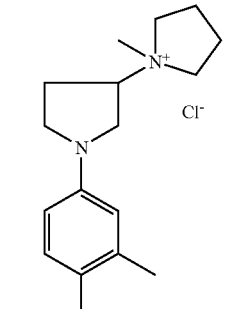 | 1'-(4-amino-3-methylphenyl)-1-methyl-[1,3*]-bipyrrolidinyl-1-ium; chloride (28) |

| Formula | Nomenclature |
|---|---|
| 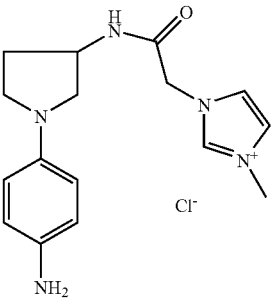 | 3-[1-(4-aminophenyl)-pyrrolidin-3-yl-carbamoyl]methyl}-1-methyl-3H-imidazol-1-ium; chloride (29) |
| 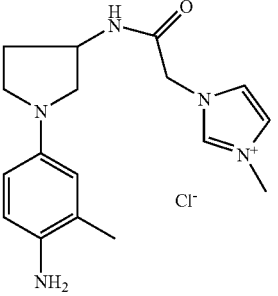 | 3-{[1-(4-amino-3-methylphenyl)-pyrrolidin-3-yl-carbamoyl]methyl}-1-methyl-3H-imidazol-1-ium; chloride (30) |
| 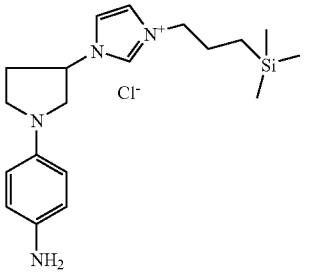 | 3-[1-(4-aminophenyl)-pyrrolidin-3-yl]-1-(3-trimethylsilanylpropyl)-3H-imidazol-1-ium; chloride (31) |
| 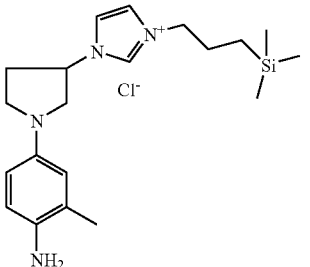 | 3-[1-(4-aminophenyl)-pyrrolidin-3-yl]-1-(3-trimethylsilanylpropyl)-3H-imidazol-1-ium; chloride (32) |
| 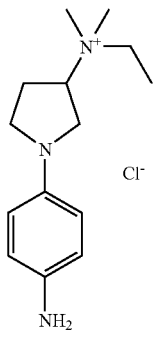 | [1-(4-aminophenyl)-pyrrolidin-3-yl]ethyl-dimethylammonium; chloride (33) |
| 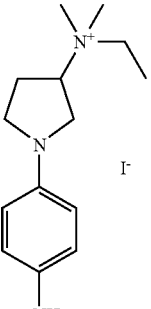 | [1-(4-aminophenyl)-pyrrolidin-3-yl]-ethyldimethyl-ammonium; iodide (34) |
| 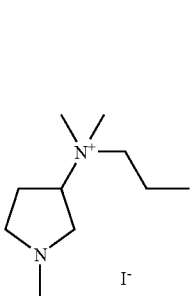 | [1-(4-aminophenyl)-pyrrolidin-3-yl]-propyldimethyl-ammonium; iodide (35) |
| 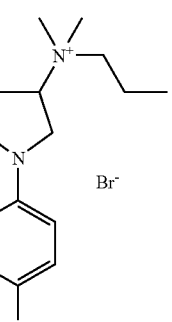 | [1-(4-aminophenyl)-pyrrolidin-3-yl]propyl-dimethylammonium; bromide (36) |
| 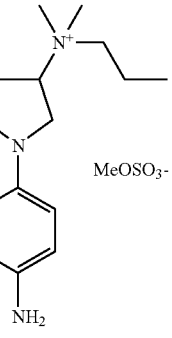 | [1-(4-aminophenyl)-pyrrolidin-3-yl]-propyldimethyl-ammonium; methosulphate (37) |

| Formula | Nomenclature |
|---|---|
| (structure) | [1-(4-aminophenyl)-pyrrolidin-3-yl]-butyldimethyl-ammonium; iodide (38) |
| (structure) | [1-(4-aminophenyl)-pyrrolidin-3-yl]-pentyldimethyl-ammonium; iodide (39) |
| (structure) | [1-(4-aminophenyl)-pyrrolidin-3-yl]-hexyldimethyl-ammonium; iodide (40) |
| (structure) | [1-(4-aminophenyl)-pyrrolidin-3-yl]-heptyldimethyl-ammonium; iodide (41) |
| (structure) | [1-(4-aminophenyl)-pyrrolidin-3-yl]-octyldimethyl-ammonium; iodide (42) |
| (structure) | [1-(4-aminophenyl)-pyrrolidin-3-yl]-decyldimethyl-ammonium; iodide (43) |
| (structure) | [1-(4-aminophenyl)-pyrrolidin-3-yl]-hexadecyldimethyl-ammonium; iodide (44) |
| (structure) | [1-(4-aminophenyl)-pyrrolidin-3-yl]-hydroxyethyldimethyl-ammonium; chloride (45) |
| (structure) | [1-(4-aminophenyl)-pyrrolidin-3-yl]-hydroxyethyldimethyl-ammonium; iodide (46) |

For the purpose of the present invention, the term "heterocyclic base" or "heterocyclic oxidation base" is intended to mean any oxidation base comprising at least one heterocyclic group, other than a pyrrolidinyl group, the nitrogen atom of which is substituted with a para-aminophenyl group and which has at least one quaternized nitrogen atom.

By way of heterocyclic oxidation bases that can be used in the compositions according to the invention, mention may be made of pyridines, pyrimidines, pyrazoles, condensed pyrazolopyrimidines, pyrazolotriazoles, pyrazolotetrazoles, pyrazolopyridazines, pyrazolothiazoles, pyrazoloimidazoles, pyrazolobenzimidazoles, pyrazoloquinolines, aminopyrrolidines, aminopyrazolines, mono- or diaminotetraquinolines, diamino- or triaminoquinolines, aminoindazoles, diaminouracils, aminoindolenines, hydrazones, julolidine or lilolidine, and also derivatives thereof and addition salts thereof.

Among the pyridine derivatives, mention may be made of the compounds described, for example, in patents GB-A-1 026 978 and GB-A-1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and addition salts thereof.

Other pyridine oxidation bases that can be used in the present invention are 3-aminopyrazolo[1,5-a]pyridines or addition salts thereof, described, for example, in Patent Application FR-A-2 801 308. By way of example, mention may be made of pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]-pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a ]pyridin-5-yl)-(2-hydroxyethyl)amino]ethanol; 2-[(3-aminopyrazolo[1,5-a]pyridin-7-yl)-(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and also addition salts thereof.

Among the pyrimidine derivatives, mention may be made of the compounds described, for example, in Patents DE-A-2359399; JP 88-169571; JP 05-63124; EP-A-0770375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethano 1,5,6-dimethylpyrazolo[1,5-a]pyrimidine-3,7-diamine, 2,6-dimethylpyrazolo[1,5-a]pyrimidine-3,7-diamine, 2,5, N7, N7-tetramethylpyrazolo[1,5-a]pyrimidine-3,7-diamine, 3-amino-5-methyl-7-imidazolylpropylaminopyrazolo[1,5-a]pyrimidine, addition salts thereof, and tautomeric forms thereof when a tautomeric equilibrium exists.

Among the pyrazole derivatives, mention may be made of the compounds described in Patents DE-A-38 43 892, DE-A-41 33 957 and Patent Applications WO 94/08969, WO 94/08970, FR-A-2 733 749 and DE-A-195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, le 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and addition salts thereof.

By way of pyrazolotriazoles, mention may be made of the compounds 3-amino-4-methyl-6-methylthio-2-phenylpyrazolo[3,2-c]-s-triazole, 3-amino-2,4,6-trimethylpyrazolo[3,2-c]-s-triazole and 3-amino-4,6-dimethylpyrazolo[3,2-c]-s-triazole. Such compounds are described in document U.S. Pat. No. 5,457,200. Mention may also be made of the compounds 7-amino-2,6-dimethylpyrazolo[1,5-b]-1,2,4-triazole, 7-amino-3,6-dimethylpyrazolo[3,2-c]-1,2,4-triazole, 7-amino-3-methylpyrazolo[3,2-c]-1,2,4-triazole, 7-amino-3-methyl-6-carboxypyrazolo-[3,2-c]-1,2,4-triazole, 7-amino-2-methylpyrazolo[1,5-b]-1,2,4-triazole, 7-amino-2-phenylpyrazolo[1,5-b]-1,2,4-triazole and 7-amino-2-methyl-6-carboxypyrazolo[1,5-b]-1,2,4-triazole. These compounds are described in Patent Application EP-A-923 929.

By way of pyrazolotetrazoles, mention may be made of the compounds 7-amino-6-methylpyrazolo[1,5-e]tetrazole, 7-amino-6-phenylpyrazolo[1,5-e]tetrazole and 7-amino-6-carboxypyrazolo[1,5-e]tetrazole, described in Patent Application EP-A-923 929.

By way of pyrazolopyridazines, mention may be made of 3-aminopyrazolo[1,5-b]pyridazine. Such compounds are described in document U.S. Pat. No. 5,457,200.

By way of pyrazolothiazoles, mention may be made of the compounds 3-amino-2-methylpyrazolo[3,2-b]thiazole, 3-aminopyrazolo[3,2-b]thiazole and 3-amino-2,5-dimethyl-6-phenylpyrazolo[3,2-b]thiazole. Such compounds are described in document U.S. Pat. No. 5,427,200.

By way of pyrazoloimidazoles, mention may be made of the compounds 3-amino-4-benzylpyrazolo[1,5-a]imidazole, 3-amino-2,4-dimethylpyrazolo[1,5-a]imidazole, 3-amino-4-methylpyrazolo[1,5-a ]imidazole. Such compounds are described in document U.S. Pat. No. 5,457,200. Mention may also be made of the compounds 7-amino-6-methylpyrazolo[1,5-a]imidazole, 7-aminopyrazolo[1,5-a]imidazole, 7-amino-2-methylpyrazolo[1,5-a]imidazole and 7-amino-2-phenylpyrazolo[1,5-a]imidazole, described in Patent Application EP-A-923 929.

By way of pyrazolobenzimidazoles, mention may be made of the compounds 7-amino-6-methylpyrazolo[1,5-a]benzimidazole, 6,7-diaminopyrazolo[1,5-a]benzimidazole, 6,7-diamino-2-methylpyrazolo[1,5-a]benzimidazole, 6,7-diamino-2-phenylpyrazolo[1,5-a]benzimidazole, described, for example, in Patent Application EP-A-923 929.

By way of pyrazoloquinolines, mention may be made of the compounds 3-amino-2-phenylpyrazolo[1,5-a]quinoline. Such compounds are described in document U.S. Pat. No. 5,457,200.

By way of aminopyrazolines, mention may be made of the compounds 1-(4'-aminophenyl)-3-aminopyrazoline, 1-(4'-hydroxyphenyl)-3-aminopyrazoline. Such compounds are described in document FR-A-2 018 056.

By way of mono- or diaminotetrahydroquinolines, mention may be made of the compounds 5-amino-1,2,3,4-tetrahydroquinoline, 5-amino-7-chloro-8-piperidino-1,2,3,4-tetrahydroquinoline, 5-amino-7-chloro-8-morpholino-1,2,3,4- tetrahydroquino line, 5,7-diamino-6-methyl-8-hydroxy-1,2,
3,4-tetrahydroquinoline, 5-amino-8-methoxy-1,2,3,4-
tetrahydroquinoline, 5-amino-7-chloro-8-dimethylamino-1,
2,3,4-tetrahydroquinoline. Such compounds are described in
document DE-A-24 41 895.

By way of diaminoquinolines, mention may be made of the
compounds 5,7-diamino-6-methyl-8-hydroxyquinoline and
5,7-diamino-2-methyl-8-hydroxyquinoline. Such compounds are described in document DE-A-24 41 598.

By way of triaminoquinolines, mention may be made of
5,7-diamino-8-methylaminoquinoline, 5,7-diamino-8-dimethylaminoquinoline, 5,7-diamino-8-morpholinoquinoline,
5,7-diamino-8-beta-hydroxyethylaminoquinoline and 5,7,8-triaminoquinoline. Such compounds are described in document DE-A-24 41 599.

By way of aminoindazoles, mention may be made of 4,7-diamino-5-methylindazole, 4,7-diamino-5,6-dimethylindazole, 6,7-diaminoindazole, 6-hydroxy-7-aminoindazole,
1-ethyl-6-hydroxy-7-aminoindazole, 6-aminoindazole, 5,6-diaminoindazole. Such compounds are described in documents FR-A-2 315 906 and DE-A-14 92 166.

By way of diaminouracils, mention may be made of the
compounds 5,6-diaminouracil, 5,6-diamino-2-thiouracil,
5,6-diamino-3-methyluracil, 5-amino-3-methyl-6-methylaminouracil, 5-amino-3-methyl-6-beta-hydroxyethylaminouracil, 5-amino-3-methyl-6-benzylaminouracil, 5-amino-3-methyl-6-phenylaminouracil, 5,6-diamino-1-phenyluracil,
5,6-diamino-1,3-dimethyluracil, 5-amino-1,3-dimethyl-6-methylaminouracil, 5-amino-1,3-dimethyl-6-beta-hydroxymethylaminouracil, 5-amino-1,3-dimethyl-6-benzylaminouracil, 5-amino-1,3-dimethyl-6-phenylaminouracil,
5-amino-1,3-dimethyl-6-dimethylaminouracil. Such compounds are described in document DE-A-25 33 629.

By way of aminoindolenines, mention may be made of the
compounds 2-methyl-5-aminoindolenine, 1-beta-hydroxyethyl-2-methyl-5-aminoindolenine. Such compounds are
described in document FR-A-1 602 547.

By way of hydrazones, mention may be made of the compounds N-methylpyridone-4-hydrazone, N-methylthiazolonehydrazone, N-methylthiazolone-2-hydrazone, N,N-dimethylbenzimidazolonehydrazone, N-methylpyridone-2-hydrazone, N-methylbenzothiazolone-2-hydrazone, 1,2-dimethylindazolone-3-hydrazone, 1,2,6-trimethylpyridone-4-hydrazone, 1-methylquinolone-2-hydrazone, 1,2,6-trimethyl-3-nitropyridone-4-hydrazone, 1,2,6-trimethyl-3-aminopyridone-4-hydrazone,
N-methylcyclohexenothiazolonehydrazone, 1,2,5-trimethylpyrazolone-3-hydrazone, 1,2-dimethylindazolone-3-hydrazone, 1,2-dimethyl-5-chloroindazolone-3-hydrazone,
1-methyl-2-ethyl-5-nitroindazolone-3-hydrazone, N-methylquinolone-4-hydrazone, N-methylbenzothiazolone-2-omega-benzenesulphonylhydrazone. Such compounds are
described in document FR-A-1 602 547.

By way of julolidine derivatives or lilolidine derivatives,
mention may be made of the compounds 9-aminojulolidine,
9-amino-8-methyljulolidine, 9-amino-8,10-dimethyljulolidine, 8-aminolilolidine. Such compounds are described in
document DE-A-24 41 597.

Preferably, the heterocyclic oxidation bases that can be
used for the present invention are chosen from pyridines,
pyrimidines, pyrazoles and pyrazolopyrimidines.

Even more preferably, they are chosen from 4,5-diaminopyrazoles.

Particularly preferably, the benzene or heterocyclic oxidation bases used in the compositions according to the invention
are chosen from cationic or noncationic para-phenylenediamines, cationic or noncationic para-aminophenols, pyrazole
derivatives, and also addition salts thereof.

Even more preferably, they are chosen from pyrazole
derivatives and addition salts thereof.

By way of benzene couplers that can be used in the compositions according to the invention, mention may be made of
meta-aminophenols, meta-phenylenediamines, meta-diphenols, and also addition salts thereof.

The meta-aminophenols that can be used, by way of benzene couplers, in the dye compositions in accordance with the
invention are preferably chosen from the compounds of formula (V) below:

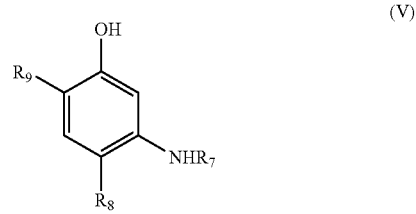

(V)

in which:
$R_7$ represents a hydrogen atom, a $C_1$-$C_4$ alkyl group, a
$C_1$-$C_4$ monohydroxyalkyl group or a $C_2$-$C_4$ polyhydroxyalkyl group;
$R_8$ represents a hydrogen atom, a $C_1$-$C_4$ alkyl group, a
$C_1$-$C_4$ alkoxyl group or a halogen atom chosen from chlorine,
bromine or fluorine;
$R_9$ represents a hydrogen atom, a $C_1$-$C_4$ alkyl group, a
$C_1$-$C_4$ alkoxyl group, a $C_1$-$C_4$ monohydroxyalkyl group, a
$C_2$-$C_4$ polyhydroxyalkyl group, a $C_1$-$C_4$ monohydroxyalkoxyl group or a $C_2$-$C_4$ polyhydroxyalkoxyl group;
and from addition salts thereof.

Among the meta-aminophenols of formula (V) above,
mention may more particularly be made of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and addition salts thereof.

The meta-phenylenediamines that can be used, by way of
benzene couplers, in the dye composition in accordance with
the invention are preferably chosen from the compounds of
formula (VI) below:

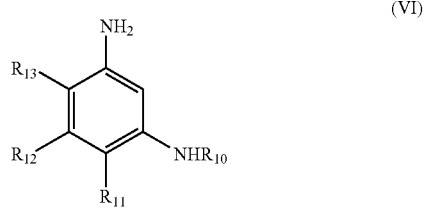

(VI)

in which:
$R_{10}$ represents a hydrogen atom, a $C_1$-$C_4$ alkyl group, a
$C_1$-$C_4$ monohydroxyalkyl group or a $C_2$-$C_4$ polyhydroxyalkyl group;
$R_{11}$ and $R_{12}$, which may be identical or different, represent
a hydrogen atom, a $C_1$-$C_4$ alkyl group, a $C_1$-$C_4$ monohydroxyalkoxyl group or a $C_2$-$C_4$ polyhydroxyalkoxyl group;

R_{13} represents a hydrogen atom, a $C_1$-$C_4$ alkoxyl group, a $C_1$-$C_4$ aminoalkoxyl group, a $C_1$-$C_4$ monohydroxyalkoxyl group, a $C_2$-$C_4$ polyhydroxyalkoxyl group or a 2,4-diaminophenoxyalkoxyl group; and from addition salts thereof.

Among the meta-phenylenediamines of formula (VI) above, mention may more particularly be made of 2,4-diaminobenzene, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy) benzene, 2,4-diamino-1-(β-hydroxyethyloxy)benzene, 2-amino-4-N-(β-hydroxyethyl)amino-1-methoxybenzene, and addition salts thereof.

The meta-diphenols that can be used, by way of benzene couplers, in the dye compositions in accordance with the invention are preferably chosen from the compounds of the formula (VII) below:

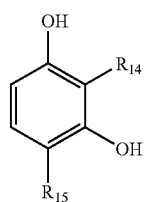
(VII)

in which:

R_{14} and R_{15}, which may be identical or different, represent a hydrogen atom, a $C_1$-$C_4$ alkyl group or a halogen atom chosen from chlorine, bromine or fluorine;
and from addition salts thereof.

Among the meta-diphenols of formula (VII) above, mention may more particularly be made of 1,3-dihydroxybenzene, 2-methyl-1,3-dihydroxybenzene, 4-chloro-1,3-dihydroxybenzene and 2-chloro-1,3-dihydroxybenzene, and addition salts thereof.

By way of heterocyclic couplers that can be used in the compositions according to the invention, mention may be made of azole-containing heterocyclic couplers, pyridine couplers, thiophenes, indolines, indoles, benzofurans, 8-amino-6-methoxyquinolines, 4-hydroxyquinolones, benzodioxoles, hydroxybenzamides, sesamol and its derivatives, benzomorpholines, and also addition salts thereof.

The azole-containing heterocyclic couplers used in the compositions according to the invention may in particular be chosen from carbazoles, hydroxyindazoles, benzoxazoles, pyrazoloazoles and pyrazolotriazoles, pyrroloazoles, imidazoloazoles, thiazoloazoles, pyrrolooxazoles, hydroxypyrazolopyrimidines, isoxazolones, indazolones and benzimidazoles.

By way of carbazoles used in the compositions of the invention, mention may be made of 1,3,6,8-tetraminocarbazole, 1,3,6,8-tetramino-9-n-propylcarbazole, 1,3,6,8-tetramino-9-β-hydroxyethylcarbazole and 1,3,6,8-tetramino-9-(2'-N,N-dimethylaminoethyl) carbazole, and addition salts thereof. These compounds are described in application DE-A-27 15 680.

By way of carbazoles, mention may also be made of 3-aminocarbazole described in application DE-A-277 496.

By way of hydroxyindazoles preferably used in the compositions according to the invention, mention may be made of the following mono hydroxyindazoles: 4-hydroxyindazole, 5-hydroxyindazole, 6-hydroxyindazole, 7-hydroxyindazole, 7-hydroxy-1-methylindazole, 4-hydroxy-6-methylindazole, 7-hydroxy-6-methylindazole, 7-hydroxy-4,6-dimethylindazole, 6-hydroxy-7-bromoindazole, 6-hydroxy-7-chloroindazole and 6-hydroxy-5,7-dichloroindazole. These hydroxyindazoles are described in Patent Application DE-A-26 23 564.

By way of benzoxazoles used in the compositions according to the invention, mention may be made of the following diaminobenzoxazoles: 5,7-diaminobenzoxazole, 5,7-diamino-2-methylbenzoxazole, 5,7-diamino-2-ethylbenzoxazole, 5,7-diamino-2-butylbenzoxazole, 5-dimethylamino-7-aminobenzoxazole, 5-amino-7-diethylaminobenzoxazole and 4,6-diaminobenzoxazole. These benzoxazoles are described in Patent Application DE-A-27 19 424.

By way of pyrazoloazoles used in the compositions according to the invention, mention may be made of pyrazolo[1,5-b]-1,2,4-triazoles, pyrazolo[3,2-c]-1,2,4-triazoles, pyrazolotetrazoles, pyrazolo[1,5-a]imidazoles, pyrazolo[1,5-e]pyrazoles and pyrazolo[1,5-e]-1,2,3-triazoles.

Preferably, the pyrazolo[1,5-b]-1,2,4-triazoles are chosen from 2-methylpyrazolo[1,5-b]-1,2,4-triazole, 2-ethylpyrazolo[1,5-b]-1,2,4-triazole, 2-isopropylpyrazolo[1,5-b]-1,2,4-triazole, 2-phenylpyrazolo[1,5-b]-1,2,4-triazole, 2,6-dimethylpyrazolo[1,5-b]-1,2,4-triazole, 6-methyl-2-ethylpyrazolo-[1, 5-1)]-1,2,4-triazole, 6-methyl-2-isopropylpyrazolo[1,5-b]-1,2,4-triazole, 6-methyl-2-phenylpyrazolo[1,5-b]-1,2,4-triazole, 6-carboxy-2-methylpyrazolo[1,5-b]-1,2,4-triazole, 6-carboxy-2-ethylpyrazolo[1,5-b]-1,2,4-triazole, 6-carboxy-2-isopropylpyrazolo[1,5-b]-1,2,4-triazole, 6-carboxy-2-phenylpyrazolo[1,5-b]-1,2,4-triazole, 6-phenyl-2-methylpyrazolo[1,5-b]-1,2,4-triazole, 6-phenyl-2-ethylpyrazolo[1,5-b]-1,2,4-triazole, 6-phenyl-2-isopropylpyrazolo[1,5-b]-1,2,4-triazole, 6-phenyl-2-phenylpyrazolo[1,5-b]-1,2,4-triazole, 6-amino-2-methylpyrazolo[1,5-b]-1,2,4-triazole, 6-amino-2-ethylpyrazolo[1,5-b]-1,2,4-triazole, 6-amino-2-isopropylpyrazolo[1,5-b]-1,2,4-triazole, 6-amino-2-phenylpyrazolo[1,5-b]-1,2,4-triazole, 6-ethylthio-2-methylpyrazolo[1,5-b]-1,2,4-triazole, 6-ethylthio-2-ethylpyrazolo[1,5-b]-1,2,4-triazole, 6-ethylthio-2-isopropylpyrazolo[1,5-b]-1,2,4-triazole, 6-ethylthio-2-phenylpyrazolo-[1,5-b]-1,2,4-triazole, 6-ethoxy-2-methylpyrazolo[1,5-b]-1,2,4-triazole, 6-ethoxy-2-ethylpyrazolo[1,5-b]-1,2,4-triazole, 6-ethoxy-2-isopropylpyrazolo[1,5-b]-1,2,4-triazole, 6-ethoxy-2-phenylpyrazolo[1,5-b]-1,2,4-triazole, 6-methyl-2-(2'-aminoethyl)pyrazolo[1,5-b]-1,2,4-triazole, 6-carboxy-2-(2'-aminoethyl)pyrazolo[1,5-b]-1,2,4-triazole, 6-phenyl-2-(2'-aminoethyl)pyrazolo[1,5-b]-1,2,4-triazole, 6-ethylthio-2-(2'-aminoethyl)pyrazolo[1,5-b]-1,2,4-triazole, 2-(2'-aminoethyl)pyrazolo[1,5-b]-1,2,4-triazole, 2-(2'-hydroxyethyl)pyrazolo[1,5-b]-1,2,4-triazole, 6-methyl-2-(2'-hydroxyethyl)pyrazolo[1,5-b]-1,2,4-triazole, 6-ethylthio-2-(2'-hydroxyethyl)pyrazolo[1,5-b]-1,2,4-triazole, 6-carboxy-2-(2'-hydroxyethyl)pyrazolo[1,5-b]-1,2,4-triazole, 6-phenyl-2-(2'-hydroxyethyl)pyrazolo[1,5-b]-1,2,4-triazole, 7-chloro-2,6-dimethylpyrazolo[1,5-b]-1,2,4-triazole, 7-bromo-2,6-dimethylpyrazolo-[1,5-b]-1,2,4-triazole, and addition salts thereof.

Preferably, the pyrazolo[3,2-c]-1,2,4-triazoles are chosen from 3-methylpyrazolo[3,2-c]-1,2,4-triazole, 3-methylsulphinyl-6-phenylpyrazolo[3,2-c]-1,2,4-triazole, 3-ethylpyrazolo[3,2-c]-1,2,4-triazole, 3-isopropylpyrazolo[3,2-c]-1,2,4-triazole, 3-phenylpyrazolo[3,2-c]-1,2,4-triazole, 3-(2'aminoethyl)pyrazolo[3,2-c]-1,2,4-triazole, 3-(2'-hydroxyethyl)pyrazolo[3,2-c]-1,2,4-triazole, 6-methyl-3-ethylpyrazolo-[3,2-c]-1,2,4-triazole, 3,6-dimethylpyrazolo[3,2-c]-1,2,4-triazole, 6-methyl-3-isopropylpyrazolo[3,2-c]-1,2,4-triazole, 6-methyl-3-phenylpyrazolo[3,2-c]-1,2,4-triazole, 6-methyl-3-(2'aminoethyl)pyrazolo-[3,2-c]-1,2,4-triazole, 6-methyl-3-(2'-hydroxyethyl)pyrazolo[3,2-c]-1,2,4-triazole, 6-methyl-3-methylthiopyrazolo[3,2-c]-1,2,4-triazole, 6-phenyl-3-methylpyrazolo[3,2-c]-1,2,4-triazole, 6-phenyl-3-ethylpyrazolo[3,2-c]-1,2,4-triazole, 6-isopropyl-3-ethylpyrazolo[3,2-c]-1,2,4-triazole, 6-phenyl-3-isopropylpyrazolo[3,2-c]-1,2,4-triazole, 6-phenyl-3-phenylpyrazolo[3,2-c]-1,2,4-triazole, 6-phenyl-3-(2' aminoethyl)pyrazolo[3,2-c]-1,2,4-triazole, 6-phenyl-3-(2'-hydroxyethyl)pyrazolo[3,2-c]-1,2,4-triazole, 6-phenyl-3-methylthiopyrazolo[3,2-c]-1,2,4-triazole, 6-ethylthio-3-methylpyrazolo[3,2-c]-1,2,4-triazole, 6-ethylthio-3-ethylpyrazolo[3,2-c]-1,2,4-triazole, 6-ethylthio-3-isopropylpyrazolo[3,2-c]-1,2,4-triazole, 6-ethylthio-3-phenylpyrazolo[3,2-c]-1,2,4-triazole, 6-ethylthio-3 (2'-aminoethyl)pyrazolo[3,2-c]-1,2,4-triazole, 6-ethylthio-3-(2'-hydroxyethyl)pyrazolo[3,2-c]-1,2,4-triazole, 6-trifluoromethyl-3-methylthiopyrazolo[3,2-c]-1,2,4-triazole, 6-trifluoromethylpyrazolo[3,2-c]-1,2,4-triazole, 6-carboxy-3-methylpyrazolo[3,2-c]-1,2,4-triazole, 6-carboxy-3-ethylpyrazolo[3,2-c]-1,2,4-triazole, 6-carboxy-3-isopropylpyrazolo[3,2-c]-1,2,4-triazole, 6-carboxy-3-phenylpyrazolo[3,2-c]-1,2,4-triazole, 6-carboxy-3-(2'-aminoethyl)pyrazolo[3,2-c]-1,2,4-triazole, 6-carboxy-3-(2'-hydroxyethyl)pyrazolo[3,2-c]-1,2,4-triazole, 7-chloro-3,6-dimethylpyrazolo[3,2-c]-1,2,4-triazole, 7-methoxycarbonyl-3,6-dimethylpyrazolo[3,2-c]-1,2,4-triazole, and addition salts thereof.

Preferably, the pyrazolotetrazoles are chosen from pyrazolo[5,1-e]tetrazole, 6-methylpyrazolo[5,1-e]tetrazole, 6-phenylpyrazolo[5,1-e]tetrazole, 6-carboxypyrazolo[5,1-e] tetrazole, 7-chloro-6-methylpyrazolo[5,1-e]tetrazole, and addition salts thereof.

Preferably, the pyrazolo[1,5-a]imidazoles are chosen from pyrazolo[1,5-a]imidazole, 2-methylpyrazolo[1,5-a]imidazole, 2-phenylpyrazolo[1,5-a]imidazole, pyrazolo[1,5-a] benzimidazole, 6-methylpyrazolo[1,5-a]imidazole, 2,6-dimethylpyrazolo[1,5-a]imidazole, 6-methyl-2-phenylpyrazolo[1,5-a]imidazole, 6-methylpyrazolo[1,5-a]-benzimidazole, 6-phenylpyrazolo[1,5-a]imidazole, 6-phenyl-2-methylpyrazolo[1,5-a]imidazole, 2,6-diphenylpyrazolo[1,5-a]imidazole, 6-phenylpyrazolo[1,5-a]benzimidazole, 6-carboxypyrazolo[1,5-a]imidazole, 6-carboxy-2-methylpyrazolo[1,5-a]imidazole, 6-carboxy-2-phenylpyrazolo[1,5-a]imidazole, 6-carboxypyrazolo[1,5-a]benzimidazole, 6-ethoxypyrazolo [1,5-a]imidazole, 6-ethoxy-2-methylpyrazolo[1,5-a]imidazole, 6-ethoxy-2-phenylpyrazolo[1,5-a ]imidazole, 6-trifluoromethylpyrazolo[1,5-a]benzimidazole, 6-aminopyrazolo[1,5-a]imidazole, 6-amino-2-methylpyrazolo[1,5-a]imidazole, 6-amino-2-phenylpyrazolo[1,5-a]imidazole, 6-aminopyrazolo[1,5-a]benzimidazole, 6-ethylthiopyrazolo[1,5-a]imidazole, 6-ethylthio-2-methylpyrazolo[1,5-a]imidazole, 6-ethylthio-2-phenylpyrazolo[1,5-a]imidazole, 7-chloro-6-methylpyrazolo[1,5-a]imidazole, 7-chloro-6-methylpyrazolo[1,5-a]benzimidazole, and addition salts thereof.

Preferably, the pyrazolo[5,1-e]pyrazoles are chosen from 8-amino-4-methylpyrazolo[5,1-e]pyrazole, 8-amino-5-chloro-4-methylpyrazolo[5,1-e]pyrazole, and addition salts thereof.

Preferably, the pyrazolo[5,1-e]-1,2,3-triazoles are chosen from 5-methylpyrazolo[5,1-e]-1,2,3-triazole, 5-methyl-6-chloropyrazolo[5,1-e]-1,2,3-triazole, 5-phenylpyrazolo[5,1-e]-1,2,3-triazole, and addition salts thereof.

These pyrazoloazoles are described in Patent Application WO 97/35551.

By way of pyrroloazoles used in the compositions according to the invention, mention may be made of pyrrolo[1,2-b]-1,2,4-triazoles, pyrrolo[2,1-c]-1,2,4-triazoles, pyrrolo[1,2-c] imidazoles, pyrrolo-[1,2-e]tetrazoles, pyrrolo[1,2-a] pyrroles, pyrrolo[1,2-a]imidazoles, pyrrolo[1,2-c]-1,2,3-triazoles, and addition salts thereof.

Preferably, the pyrrolo[1,2-b]-1,2,4-triazoles are chosen from 3,4-dicyano-8-methylpyrrolo[1,2-b]-1,2,4-triazole, 3,4-dicyano-8-phenylpyrrolo[1,2-b]-1,2,4-triazole, 3,4-dicyano-8-tert-butylpyrrolo[1,2-b]-1,2,4-triazole, 5-chloro-3,4-dicyano-8-methylpyrrolo[1,2-b]-1,2,4-triazole and also 5-cyano-4-ethoxycarbonyl-8-methylpyrrolo[1,2-b]-1,2,4-triazole, 5-cyano-4-carboxy-8-methylpyrrolo[1,2-b]-1,2,4-triazole, 4,5-dicyano-8-methylpyrrolo[1,2-b]-1,2,4-triazole, 5-cyano-8-methyl-4-phenylpyrrolo[1,2-b]-1,2,4-triazole, 4,8-dimethylpyrrolo[1,2-b]-1,2,4-triazole, 4,5-di(ethoxycarbonyl)-8-methylpyrrolo[1,2-b]-1,2,4-triazole, 3-chloro-5-cyano-4-ethoxycarbonyl-8-methylpyrrolo[1,2-b]-1,2,4-triazole, 5-cyano-4-ethoxycarbonyl-8-phenylpyrrolo[1,2-b]-1,2,4-triazole, 5-cyano-4-carboxy-8-phenylpyrrolo[1,2-b]-1,2,4-triazole, 4,5-dicyano-8-phenylpyrrolo[1,2-b]-1,2,4-triazole, 4,5-di(ethoxycarbonyl)-8-phenylpyrrolo[1,2-b]-1,2,4-triazole, 3-chloro-5-cyano-4-ethoxycarbonyl-8-phenypyrrolo[1,2-b]-1,2,4-triazole, 4-cyano-5-carboxy-8-(2-nitro-5-hydroxyphenyl)pyrrolo[1,2-b]-1,2,4-triazole, and addition salts thereof.

Preferably, the pyrrolo[2,1-c]-1,2,4-triazoles are chosen from 5,6-dicyano-3-methylpyrrolo[2,1-c]-1,2,4-triazole, 7-chloro-5,6-dicyano-3-methylpyrrolo[2,1-c]-1,2,4-triazole, and also 6,7-dicyano-3-methylpyrrolo[2,1-c]-1,2,4-triazole, 5-chloro-6,7-dicyano-3-methylpyrrolo[2,1-c]-1,2,4-triazole, 6,7-di(ethoxycarbonyl)-3-methylpyrrolo[2,1-c]-1,2,4-triazole, 7-cyano-3-methyl-6-phenylpyrrolo-[2,1-c]-1,2,4-triazole, 7-cyano-3-methyl-6-tert-butylpyrrolo-[2,1-c]-1,2,4-triazole, and addition salts thereof.

Preferably, the pyrrolo[1,2-c]imidazoles are chosen from 6,8-dicyano-5-ethoxycarbonylpyrrolo[1,2-c]imidazole, 4-chloro-6,8-dicyano-5-ethoxycarbonylpyrrolo[1,2-c]imidazole, and addition salts thereof.

Preferably, the pyrrolo[1,2-e]tetrazoles are chosen from 6,7-dicyanopyrrolo[1,2-e]tetrazole, 6-cyano-7-ethoxycarbonylpyrrolo[1,2-e]tetrazole, 5-chloro-6,7-dicyanopyrrolo[1,2-e]tetrazole, and addition salts thereof.

Preferably, the pyrrolo[1,2-a]imidazoles are chosen from 2,3,7-tricyano-6-methylpyrrolo[1,2-a]imidazole, 2,3,7-tricyano-6-trifluoromethylpyrrolo[1,2-a]imidazole, 2,3,7-tricyano-6-tert-butylpyrrolo[1,2-a]imidazole, 2,3,7-tricyano-6-phenylpyrrolo[1,2-a]imidazole, 2,3,7-tricyano-6-ethoxycarbonylpyrrolo[1,2-a]imidazole, 5-chloro-2,3,7-tricyano-6-tert-butylpyrrolo[1,2-a]imidazole, 5-chloro-2,3,7-tricyano-6-phenylpyrrolo[1,2-a]imidazole, 7-cyano-6-ethoxycarbonylpyrrolo[1,2-a]benzimidazole, 7-cyano-6-phenylpyrrolo[1,2-a]benzimidazole, 7-amido-6-ethoxycarbonylpyrrolo[1,2-a]benzimidazole, and addition salts thereof.

Preferably, the pyrrolo[1,2-c]-1,2,3-triazoles are chosen from 5,6,8-tricyanopyrrolo[1,2-c]-1,2,3-triazole, 5,8-dicyano-6-ethoxycarbonylpyrrolo[1,2-c]-1,2,3-triazole, 4-chloro-5,8-dicyano-6-ethoxycarbonylpyrrolo[1,2-c]-1,2,3-triazole, and addition salts thereof.

These pyrroloazoles are described in Patent Application WO 97/35554.

By way of imidazoloazoles used in the compositions according to the invention, mention may be made of imidazolo[3,2-a]imidazoles, imidazolo[1,2-b]-1,2,4-triazoles, imidazolo[2,1-c]-1,2,4-triazoles, and addition salts thereof.

Preferably, the imidazolo[3,2-a]imidazoles are chosen from 7,8-dicyano imidazolo[3,2-a]imidazole, 7,8-dicyano-4-methylimidazolo[3,2-a]imidazole, 7,8-dicyano-4-ethyl-imidazolo[3,2-a]imidazole, 7,8-dicyano-4-isopropylimidazolo[3,2-a]imidazole, 7,8-dicyano-4-phenylimidazolo[3,2-a]imidazole, 5-chloro-7,8-dicyano-4-methylimidazolo[3,2-a]imidazole, 7,8-dicyano-4-trifluoromethylimidazolo[3,2-a]imidazole, and addition salts thereof.

Preferably, the imidazolo[1,2-b]-1,2,4-triazoles are chosen from imidazolo[1,2-b]-1,2,4-triazole, 6-methylimidazolo-[1,2-b]-1,2,4-triazole, 6-isopropylimidazolo[1, 2-1)]-1,2,4-triazole, 6-phenylimidazolo[1,2-b]-1,2,4-triazole, 2,6-dimethylimidazolo[1,2-b]-1,2,4-triazole, 6-isopropyl-2-methylimidazolo[1,2-b]-1,2,4-triazole, 2-methyl-6-phenylimidazolo[1,2-b]-1,2,4-triazole, 6-methyl-2-phenylimidazolo[1,2-b]-1,2,4-triazole, 6-isopropyl-2-phenylimidazolo[1,2-b]-1,2,4-triazole, 7-chloro-2,6-dimethylimidazolo[1,2-b]-1,2,4-triazole, 7-chloro-2-phenyl-6-tert-butylimidazolo[1,2-b]-1,2,4-triazole, 6-trifluoromethylimidazolo[1,2-b]-1,2,4-triazole, and addition salts thereof.

Preferably, the imidazolo[2,1-c]-1,2,4-triazoles are chosen from imidazolo[2,1-c]-1,2,4-triazole, 5-methylimidazolo[2,1-c]-1,2,4-triazole, 5,8-dimethylimidazolo[2,1-c]-1,2,4-triazole, 5-methyl-8-phenylimidazolo[2,1-c]-1,2,4-triazole, 8-phenylimidazolo[2,1-c]-1,2,4-triazole, 6-chloro-5,8-dimethylimidazolo[2,1-c]-1,2,4-triazole, and addition salts thereof.

These imidazoloazoles are described in Patent Application WO 97/35552.

The thiazoloazoles are described in Patent Application FR-A-2 752 524.

By way of pyrrolooxazoles used in the compositions according to the invention, mention may be made of the compositions described, in general, in Patent Application FR-A-2 752 522, and addition salts thereof.

By way of hydroxypyrazolopyrimidines used in the compositions according to the invention, mention may be made of hydroxypyrazolo[1,5-a]pyrimidines, and more particularly 2-hydroxy-5-methyl-7-ethylpyrazolo[1,5-a]pyrimidine, 2-hydroxy-5,6,7-trimethylpyrazolo[1,5-a]pyrimidine, 2-hydroxy-5,7-dimethyl-6-ethylpyrazolo-[1,5-a]pyrimidine, 2-hydroxy-7-methylpyrazolo[1,5-a]pyrimidine, 2-hydroxy-5-methyl-7-carboxypyrazolo[1,5-a]pyrimidine, 2,7-dihydroxy-5,6-dimethylpyrazolo[1,5-a]pyrimidine, and addition salts thereof. These hydroxypyrazolopyrimidines are described in Patent Application DE-A-40 29 324.

By way of isoxazolones used in the compositions according to the invention, mention may be made of 4-carboxy-β,γ-benzoisoxazolone, 1-acetyl-4-carboxy-β,γ-benzoisoxazolone, 6-carboxy-β,γ-benzoisoxazolone, 1-acetyl-6-carboxy-β,γ-benzoisoxazolone, β,γ-benzoisoxazolone, 1-acetyl-β,γ-benzoisoxazolone, 4-methyl-β,γ-benzoisoxazolone, 1-acetyl-4-(β-hydroxyethylamino)carbonyl-β,γ-benzoisoxazolone, 3-phenylisoxazol-5-one, 2-acetyl-3-phenylisoxazol-5-one, 3,4-diphenylisoxazol-5-one, 3-methylisoxazol-5-one, 3,4-tetramethyleneisoxazol-5-one, and addition salts thereof.

These isoxazolones are described in Patent Application FR-A-2 040 260.

By way of indazolones used in the compositions according to the invention, mention may be made of indazolone, 5-chloroindazolone, 6-chloroindazolone, 1-ethylindazolone, 5-dimethylaminoindazolone, 1-methylindazolone, 1-isopropylindazolone, 1-butylindazolone, 3-chloroindazolone, 4-chloroindazolone, 5-methylindazolone, 6-methylindazolone, 5-ethylindazolone, 6-propylindazolone, 5-butylindazolone, 1,5-dimethylindazolone, 1,6-dimethylindazolone, 1-methyl-5-chloroindazolone, 1-methyl-6-chloroindazolone, 1-ethyl-5-chloroindazolone, 1-ethyl-6-bromo-indazolone, 5-aminoindazolone, 6-dimethylaminoindazolone, 5-diethylaminoindazolone, 1-methyl-5-dimethylaminoindazolone 5-dibutylaminoindazolone, 1-ethyl-5-dipropylaminoindazolone, and addition salts thereof.

These indazolones are described in Patent Application DE-A-26 32 390.

By way of benzimidazoles used in the compositions according to the invention, mention may be made of 4,7-dihydroxybenzimidazole, 4,7-dihydroxy-1-methylbenzimidazole, 4,7-dihydroxy-2-methylbenzimidazole, 4,7-dihydroxy-1-ethylbenzimidazole, 4,7-dihydroxy-1-propylbenzimidazole, 4,7-dihydroxy-1-butylbenzimidazole, 4,7-dihydroxy-2-ethylbenzimidazole, 4,7-dihydroxy-2-butylbenzimidazole, 4,7-dihydroxy-1,2-dimethylbenzimidazole, 4,7-dimethoxybenzimidazole, le 4,7-dimethoxy-1-methylbenzimidazole, 4,7-dimethoxy-1-ethylbenzimidazole, 4,7-dimethoxy-2-methylbenzimidazole, 4,7-dimethoxy-2-ethylbenzimidazole, 5,6-dihydroxybenzimidazole, 5,6-dihydroxy-1-methylbenzimidazole, 5,6-dihydroxy-1-ethylbenzimidazole, 5,6-dihydroxy-1-butylbenzimidazole, 5,6-dihydroxy-2-methylbenzimidazole, 5,6-dihydroxy-2-butylbenzimidazole, 5,6-dihydroxy-2-phenylbenzimidazole, 5,6-dimethoxybenzimidazole, 5,6-dimethoxy-1-methylbenzimidazole, 5,6-dimethoxy-1-ethylbenzimidazole, 5,6-dimethoxy-1-propylbenzimidazole, 5,6-dimethoxy-2-methylbenzimidazole, 5,6-dimethoxy-2-butylbenzimidazole, 5,6-dimethoxy-2-phenylbenzimidazole, 5,6-dimethoxy-1,2-dimethylbenzimidazole, 4-hydroxy-7-methoxybenzimidazole, 5-hydroxy-6-methoxybenzimidazole, 4-hydroxy-7-methoxy-1-methylbenzimidazole, 5-hydroxy-6-methoxy-1,2-dimethylbenzimidazole. These benzimidazoles are described in Patent Application DE-A-28 12 678.

By way of benzimidazoles used in the compositions according to the invention, mention may also be made of ω-cyanoacetylbenzimidazoles, described in general in application DE-A-24 46 632, and in particular 5-amino-1-methyl-2-(ω-cyanoacetyl)benzimidazole, and also addition salts thereof.

By way of pyridine couplers used in the compositions according to the invention, mention may be made of 2-amino-3-hydroxypyridine, 2,3-diaminopyridines, 3-amino-5-hydroxypyridines, and addition salts thereof.

By way of 2,3-diaminopyridines used in the compositions according to the invention, mention may be made of 6-methoxy-3-amino-2-phenylaminopyridine, 6-methoxy-3-amino-2-(4'-hydroxyphenyl)pyridine, 6-methoxy-3-amino-2-(2'-methoxyphenyl)aminopyridine, 6-methoxy-3-amino-2-(2'-hydroxyphenyl)aminopyridine, 6-methoxy-3-amino-2-diethylaminopyridine, 6-methoxy-3-amino-2-dimethylaminopyridine, 6-methoxy-3-amino-2-(methyl-, 2'-hydroxyethyl)aminopyridine, 6-methoxy-3-amino-2-(n-butyl-, 2'-hydroxyethyl)pyridine, 6-methoxy-3-amino-2-bis-(2'-hydroxyethyl)aminopyridine, 6-methoxy-3-amino-2-(2', 3'-dihydroxypropyl)aminopyridine, 6-methoxy-3-amino-2-(1',1'-dimethyl-2'-hydroxyethyl)aminopyridine, 6-methoxy-3-amino-2-(1'-hydroxymethyl-2'-hydroxyethyl)

aminopyridine, 6-methoxy-3-amino-2-(1'-methyl-2'-hydroxyethyl)aminopyridine, 6-methoxy-3-amino-2-(3'-dimethylaminopropyl)aminopyridine, 6-methoxy-3-amino-2-bis(methoxyethyl)aminopyridine, 6-methoxy-3-amino-2-bis(2'-propenyl)aminopyridine, 6-methoxy-3-amino-2-pyrrolidinylpyridine, 6-methoxy-3-amino-2-(3'-acetamidopyrrolidinyl)pyridine, 6-methoxy-3-amino-2-(2',5'-dimethylpyrrolidinyl)pyridine, 6-methoxy-3-amino-2-(2'-dimethylamino ethyl)aminopyridine, 6-methoxy-3-amino-2-morpholinopyridine, 6-methoxy-3-amino-2-(2'-methylpyrrolidinyl)pyridine, 6-methoxy-3-amino-2-piperazinylpyridine, 6-methoxy-3-amino-2-pyridinylpyridine, 6-methoxy-3-amino-2-pyrrolidinylpyridine, 6-methoxy-3-amino-2-(2'-methylpyridinyl)pyridine, 6-methoxy-3-amino-2-(2'-hydroxyethylpyridinyl)pyridine, 6-methoxy-3-amino-2-(2'-pyrrolidinylethyl)aminopyridine, 6-methoxy-3-amino-2-(3'-imidazolinylpropyl)aminopyridine, 6-methoxy-3-amino-2-(3'-(3"-methylimidazolium)propyl)aminopyridine, 6-(2'-trifluoroethoxy)-5-trifluoromethyl-2,3-diaminopyridine, 6-phenoxy-5-trifluoromethyl-2,3-diaminopyridine, 6-methoxy-2,3-diaminopyridine, and addition salts thereof.

Preferably, among the latter compounds, the pyridine coupler is chosen from the compounds 6-methoxy-3-amino-2-hydroxyethylaminopyridine, 6-methoxy-3-amino-2-(2',3'-dihydroxypropyl)aminopyridine, 6-methoxy-3-amino-2-(1'-methyl-2'-hydroxyethyl)aminopyridine, 6-methoxy-3-amino-2-pyrrolidinylpyridine, 6-methoxy-3-amino-2-(2'-methylpyrrolidinyl)pyridine, 6-methoxy-3-amino-2-(2'-methylpyridinyl)pyridine, 6-methoxy-3-amino-2-(2'-hydroxyethylpyridinyl)pyridine, 6-methoxy-2,3-diaminopyridine, and addition salts thereof.

These couplers may be prepared according to methods that are known and described in the literature. By way of examples, reference may be made to Patent Application DE-A-32 33 540.

By way of 3-amino-5-hydroxypyridines used in the compositions according to the invention, mention may be made of 3-amino-5-hydroxy-2,6-dimethoxypyridine, 3-amino-5-hydroxy-2,6-di-(2'-hydroxyethyloxy)pyridine, and addition salts thereof. These 3-amino-5-hydroxypyridines are described in Patent Application DE-A-34 42 128.

By way of pyridine couplers, use will preferably be made of 2-amino-3-hydroxypyridine and addition salts thereof.

By way of thiophenes used in the compositions according to the invention, mention may be made of ω-cyanoacetylthiophenes, described in general in application DE-A-24 46 632, and in particular 5-amino-2-(ω-cyanoacetyl)thiophene, and also addition salts thereof.

By way of indolines used in the compositions according to the invention, mention may be made of 5-aminoindolines, 6-aminoindolines, 7-aminoindolines, 4-hydroxyindoline, 5-hydroxyindoline, 6-hydroxyindoline, 5,6-dihydroxyindoline, 5,6-diaminoindoline and 5,7-diaminoindoline, 5-amino-6-nitroindoline, 5-bromo-7-nitroindoline, 6-nitroindoline, and addition salts thereof, and in particular hydrochlorides thereof. These indolines are described in U.S. Pat. No. 4,013,404.

Among the 5,7-diaminoindolines, mention may be made of: 5,7-diamino-1-methylindoline, 5,7-diamino-2-methylindoline, 5,7-diamino-3-methylindoline, 5,7-diamino-2,2-dimethylindoline, 5,7-diamino-2,3-dimethylindoline, 5,7-diamino-2-methyl-3-ethylindoline, 5,7-diamino-1-ethyl-2-methyl-2-ethylindoline, 5,7-diamino-6-methylindoline, 5,7-diamino-1,6-dimethylindoline, 5-dimethylamino-7-amino-1-butylindoline, la 5-diethylamino-7-amino-2,2-dipropylindoline, 5-amino-7-dimethylamino-2-methyl-3-butylindoline, 5-amino-7-dibutylamino-3,3-diethylaminoindoline, 5,7-bisdimethylaminoindoline, and addition salts thereof. These indolines are described in Patent Application DE-A-27 16 671.

Mention may also be made of the following indolines and salts thereof: 6-aminoindoline, 6-hydroxyindoline, 1-ethyl-6-aminoindoline, 1-N-ethyl-4-hydroxyindoline. These indolines are described in Patent Application DE-A-19 16 139.

Among the 5,6-dihydroxyindolines, mention may be made of: 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 2-carboxy-5,6-dihydroxyindoline, and addition salts thereof. These indolines are described in Patent Application WO 01/93818.

By way of indoles used in the compositions according to the invention, mention may be made of 6-hydroxyindole and its derivatives, 5,6-dihydroxyindole and its derivatives, 4-hydroxyindole and its derivatives, and also addition salts thereof. Preferably, the indole coupler is 6-hydroxyindole.

By way of benzofurans used in the compositions according to the invention, mention may be made of hydroxybenzofurans, diaminobenzofurans, ω-cyanoacetylbenzofurans, and addition salts thereof.

Preferably, the hydroxybenzofurans used are 2-methyl-6-hydroxybenzofuran, 3-methyl-6-hydroxybenzofuran, 2,4-dimethyl-6-hydroxybenzofuran, 3-n-propyl-6-hydroxybenzofuran, 2-ethyl-5-hydroxybenzofuran, 2-methyl-5-hydroxybenzofuran, 3-methyl-5-hydroxybenzofuran, 3-isobutyl-5-hydroxybenzofuran, 3-ethyl-5-hydroxybenzofuran, 2,6-dimethyl-5-hydroxybenzofuran, 3,6-dimethyl-5-hydroxybenzofuran, 6,7-dimethyl-5-hydroxybenzofuran, 3-n-propyl-5-hydroxybenzofuran, 3-methyl-4-n-propyl-5-hydroxybenzofuran, 2-hexyl-5-hydroxybenzofuran, 2-n-propyl-5-hydroxybenzofuran, 4-tert-butyl-5-hydroxybenzofuran, 6-tert-butyl-5-hydroxybenzofuran, 4-methyl-5-hydroxybenzofuran, 3-methyl-5-n-propyl-4-hydroxybenzofuran, 2-ethyl-4-hydroxybenzofuran, 2-methyl-6-pentyl-4-hydroxybenzofuran, 6-pentyl-4-hydroxybenzofuran, 3,5-dimethyl-4-hydroxybenzo furan, 3,7-dimethyl-4-hydroxybenzofuran, 2,6-di-tert-butyl-4-hydroxybenzofuran, 2-methyl-4-hydroxybenzofuran, 3-methyl-4-hydroxybenzofuran, 2-methyl-7-ethyl-4-hydroxybenzofuran, 2,7-dimethyl-4-hydroxybenzofuran, 2-isopropyl-4-hydroxybenzofuran, 3-ethyl-4-hydroxybenzofuran, 3-methyl-7-tert-butyl-4-hydroxybenzofuran, 3-methyl-5-tert-butyl-4-hydroxybenzofuran, 2,6-dimethyl-4-hydroxybenzofuran, 3-isopropyl-4-hydroxybenzofuran, 3-n-propyl-4-hydroxybenzofuran, 3-methyl-7-n-propyl-4-hydroxybenzofuran, 3-methyl-6-n-propyl-7-hydroxybenzofuran, 3-methyl-7-hydroxybenzofuran, 2-ethyl-4-methyl-7-hydroxybenzofuran, 2-ethyl-5-methyl-7-hydroxybenzofuran, and addition salts thereof. These hydroxybenzofurans are described in Patent Application EP-A-0 506 549.

Preferably, the diaminobenzofurans used are 5,7-diaminobenzofuran, 5,7-diamino-2-methylbenzofuran, 5,7-diamino-2-ethylbenzofuran, 5-dimethylamino-7-aminobenzofuran, 4,6-diaminobenzofuran, and addition salts thereof. These diaminobenzofurans are described in Patent Application DE-A-27 19 424.

Preferably, the ω-cyanoacetylbenzofurans used are the ω-cyanoacetylbenzofurans described in general in application DE-A-24 46 632, and in particular 5-amino-2-(ω-cyanoacetyl)benzofuran, and also addition salts thereof.

By way of 8-amino-6-methoxyquinolines used in the compositions according to the invention, mention may be made of 8-amino-6-methoxyquinoline, 8-amino-5-bromo-6-methoxyquinoline, 8-amino-5-chloro-6-methoxyquinoline, 8-amino-5,7-dibromo-6-methoxyquino line, 8-amino-5-methyl-6-methoxyquinoline, 8-amino-5,7-dimethyl-6-methoxyquinoline, 8-amino-5-ethyl-6-methoxyquinoline, 8-amino-5-butyl-6-methoxyquinoline, 8-amino-5-phenyl-6-methoxyquinoline, 8-amino-2-phenyl-6-methoxyquinoline, 8-amino-2-benzyloxy-6-methoxyquinoline, 8-amino-4-dimethylamino-6-methoxyquinoline, 8,4-diamino-6-methoxyquinoline, 8-amino-4-chloro-6-methoxyquinoline, and addition salts thereof. These 8-amino-6-methoxyquinolines are described in Patent Application DE-A-26 26 141.

By way of 4-hydroxyquinolones used in the compositions according to the invention, mention may be made of 7-dimethylamino-4-hydroxy-2-quinolone, 6-methyl-4-hydroxy-2-quinolone, 6-dimethylamino-4-hydroxy-2-quinolone, 6-methoxy-4-hydroxy-2-quinolone, 8-chloro-4-hydroxy-2-quinolone, 1-methyl-7-dimethylamino-4-hydroxy-2-quinolone, 1-methyl-4-hydroxy-2-quinolone, 1-methyl-8-chloro-4-hydroxy-2-quinolone, 1,6-dimethyl-4-hydroxy-2-quinolone, 1-methyl-6-dimethylamino-4-hydroxy-2-quinolone, 6-(2-hydroxyethyl)-4-hydroxy-2-quinolone, 1-isopropyl-4-hydroxy-2-quinolone, 1-methyl-7-isopropyl-4-hydroxy-2-quinolone, 1-n-butyl-8-bromo-4-hydroxy-2-quinolone, and addition salts thereof. These 4-hydroxyquinolones are described in Patent Application DE-A-23 34 738.

By way of benzodioxoles used in the compositions according to the invention, mention may be made of the compounds described, in general, in Patent Applications DE-A-197 18 534 and DE-A-28 13 076.

Preferably, the benzodioxoles used are 5-amino-1,3-benzodioxole, 5-hydroxy-1,3-benzodioxole, 5-amino-2-methyl-1,3-benzodioxole, 5-hydroxy-2,2-dimethyl-1,3-benzodioxole, 5-hydroxy-2-ethyl-1,3-benzodioxole, 5-hydroxy-2-butyl-1,3-benzodioxole, 5-hydroxy-2-phenyl-1,3-benzodioxole, 5,6-dihydroxy-1,3-benzodioxole, 4,7-dihydroxy-1,3-benzodioxole, 4,7-diamino-2-methyl-1,3-benzodioxole, 5,6-diamino-2,2-diphenyl-1,3-benzodioxole, 4,5,7-triamino-1,3-benzodioxole, 5-hydroxy-7-methyl-2,2-diethyl-1,3-benzodioxole, and addition salts thereof with an acid, described in Patent Application DE-A-28 13 076.

By way of hydroxybenzamides used in the compositions according to the invention, mention may be made of 2,4-dihydroxybenzamides, and in particular N-phenyl-2,4-dihydroxybenzamide, N-(2'-methoxyphenyl)-2,4-dihydroxybenzamide, N-(3'-methoxyphenyl)-2,4-dihydroxybenzamide, N-(4'-methoxyphenyl)-2,4-dihydroxybenzamide, N-(4'-carboxyphenyl)-2,4-dihydroxybenzamide, N-(2'-pyridyl)-2,4-dihydroxybenzamide, N-(3'-pyridyl)-2,4-dihydroxybenzamide, N-(2',5'-dimethoxyphenyl)-2,4-dihydroxybenzamide, N-(3',5'-dimethoxyphenyl)-2,4-dihydroxybenzamide, N-(2'-methoxy-5'-aminophenyl)-2,4-dihydroxybenzamide, N-(4'-(N,N-dimethylamino)phenyl)-2,4-dihydroxybenzamide, N-(4'-hydroxyphenyl)-2,4-dihydroxybenzamide, N-methyl-2,4-dihydroxybenzamide, N-benzyl-2,4-dihydroxybenzamide, unsubstituted 2,4-dihydroxybenzamide, and addition salts thereof. These hydroxybenzamides are described in Patent Application DE-A-38 22 449.

By way of sesamol derivatives used in the compositions according to the invention, mention may be made, in addition to sesamol, of 1-N-β-hydroxyethylamino-3,4-methylenedioxybenzene.

By way of benzomorpholines used in the compositions according to the invention, mention may be made of 6-hydroxybenzomorpholine, 6-aminobenzomorpholine, and addition salts thereof.

By way of a naphthalene coupler or couplers that can be used in the compositions according to the invention, mention may be made of alpha-naphthol, the substituted naphthalenes of formula (VIII) below, and addition salts thereof:

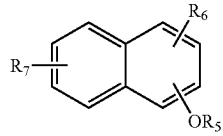

(VIII)

in which:

$R_5$ represents a hydrogen atom or a —CO—R group in which R represents a $C_1$-$C_4$ alkyl group;

$R_6$ represents a hydrogen atom, a hydroxyl group, a $C_1$-$C_4$ alkyl group or an —$SO_3H$ group;

$R_7$ represents a hydrogen atom or a hydroxyl group;

it being understood that at least one of groups $R_5$ to $R_7$ is other than a hydrogen atom.

Among the naphthalene couplers that can preferably be used in the dye compositions in accordance with the invention, mention may in particular be made of:

alpha-naphthol,
1,7-dihydroxynaphthalene,
2,7-dihydroxynaphthalene,
2,5-dihydroxynaphthalene,
2,3-dihydroxynaphthalene,
1-acetoxy-2-methylnaphthalene,
1-hydroxy-2-methylnaphthalene,
1-hydroxy-4-naphthalenesulphonic acid,
and addition salts thereof.

Particularly preferably, the oxidation couplers used in the compositions according to the invention are chosen from meta-aminophenols, meta-phenylenediamines, meta-diphenols, indolines, indoles, and also addition salts thereof.

Preferably, the oxidation dye(s) of the invention is (are) chosen from benzene or heterocyclic oxidation dyes.

The oxidation bases and oxidation couplers may be present in the compositions of the invention in the form of addition salts, and in particular in the form of addition salts with an acid.

The addition salts with an acid that can be used in the context of the invention are in particular chosen from hydrochlorides, hydrobromides, sulphates, citrates, succinates, tartrates, lactates, acetates, alkyl sulphates and alkyl sulphonates.

When the oxidation bases or the oxidation couplers contain one or more carboxylic or sulphonic acid functions, addition salts with a base can be envisaged. The addition salts with a base that can be used in the context of the dye compositions of the invention are then in particular those obtained with sodium hydroxide, potassium hydroxide, aqueous ammonia or amines.

The concentration of oxidation dye(s) of the compositions according to the present application preferably ranges from 0.005% to 15% by weight, in particular from 0.01% to 10% by weight, and more preferably from 0.5% to 5% by weight, relative to the total weight of the composition.

The dye composition in accordance with the invention may, in addition, contain one or more direct dye(s) that can in particular be chosen from nitrobenzene dyes, azo direct dyes, methine direct dyes, and addition salts thereof. These direct dyes may be nonionic, anionic or cationic in nature.

The medium used in the compositions according to the present invention is an aqueous medium or a medium containing water and at least one organic solvent.

The organic solvent(s) used in the compositions according to the invention may be chosen from monohydroxylated alcohols and polyols.

By way of monohydroxylated alcohols that can be used, mention may be made of $C_1$-$C_4$ lower alcohols such as ethanol, isopropanol, tert-butanol or n-butanol, and mixtures thereof. The alcohol used is preferably ethanol.

By way of polyols that can be used, mention may be made of propylene glycol, polyethylene glycols, polyol ethers such as 2-butoxy-ethanol, propylene glycol monomethyl ether, diethylene glycol monoethyl ether and diethylene glycol monomethyl ether, and also aromatic alcohols such as benzyl alcohol or phenoxyethanol, and mixtures thereof.

The concentration of organic solvent(s) in the compositions according to the present invention is preferably between 0 and 30% by weight, and more preferably between 0 and 20% by weight, relative to the total weight of the composition.

The dye composition in accordance with the invention may also contain one or more adjuvants conventionally used in compositions for dyeing the hair, such as additional anionic, cationic, nonionic, amphoteric or zwitterionic surfactants—other than the sorbitan fatty acid esters of the invention—, or mixtures thereof; additional nonionic, amphoteric, zwitterionic, anionic or cationic polymers—other than the cationic cellulose ethers used in the compositions according to the invention—, or mixtures thereof; antioxidants; penetrating agents; sequestrant agents; fragrances; buffers; dispersants; conditioning agents such as, for example, modified or unmodified, volatile or non-volatile silicones; film-forming agents; ceramides; preservatives; opacifiers; vitamins; amino acids; oligopeptides; peptides; modified or unmodified, hydrolysed or nonhydrolysed proteins; enzymes; branched or unbranched fatty acids and fatty alcohols; animal, plant or mineral waxes; hydroxylated organic acids; UV screens; antioxidants and free-radical scavengers; anti-dandruff agents; agents for regulating seborrhoea; calmatives; mineral, plant or animal oils; polyisobutenes and poly(α-olefins); pigments; acids, bases, plasticizers, mineral fillers, pearlescent agents, flakes; antistatic agents and reducing agents.

The adjuvant(s) above is (are), in general, present in an amount, for each of them, of preferably between 0.01% and 40% by weight, and more preferably between 0.1% and 20% by weight, relative to the weight of the composition.

The compositions according to the present application may also contain, as additional cosmetic adjuvant, at least one thickener, also referred to as "rheology-adjusting agent".

The rheology-adjusting agent(s) may be chosen from mineral or organic thickeners, and in particular polymeric associative thickeners, fatty alcohols (oleyl alcohol), additional cellulosic derivatives—different from the cellulose ethers according to the invention—(hydroxyethylcellulose, hydroxypropylcellulose, carboxymethylcellulose) and gums of microbial origin (xanthan gum, scleroglucan gum).

The preferred rheology-adjusting agent(s) is (are) chosen from fatty alcohols, nonionic cellulose ethers and gums of microbial origin.

The concentration of thickener(s) is preferably between 0.01% and 20% by weight, and even more preferably between 1% and 10% by weight, relative to the total weight of the composition.

Of course, those skilled in the art will take care to select this (or these) possible additional compound(s) in such a way that the advantageous properties intrinsically associated with the oxidation dyeing composition in accordance with the invention are not, or are not substantially, impaired by the addition (s) envisaged.

The pH of the dye composition in accordance with the invention generally ranges from 3 to 12 approximately, and preferably from 5 to 11 approximately. It may be adjusted to the desired value by means of acidifying or basifying agents commonly used in the dyeing of keratin fibres or alternatively using a conventional buffer system or conventional buffer systems.

Among the acidifying agents, mention may, by way of example, be made of mineral or organic acids such as hydrochloric acid, orthophosphoric acid, sulphuric acid, sulphonic acids and carboxylic acids, for instance acetic acid, tartaric acid, citric acid and lactic acid.

Among the basifying agents, mention may, by way of example, be made of aqueous ammonia, alkali metal carbonates, alkali metal silicates and metasilicates, alkanolamines such as mono-, di- and triethanolamines and derivatives thereof, sodium hydroxide or potassium hydroxide and the compounds of formula (IX) below:

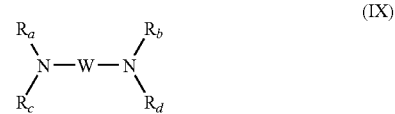

in which:

W is a propylene residue optionally substituted with a hydroxyl group or a $C_1$-$C_4$ alkyl group;

$R_a$, $R_b$, $R_c$, and $R_d$, which may be identical or different, represent a hydrogen atom, a $C_1$-$C_4$ alkyl group or a $C_1$-$C_4$ hydroxyalkyl group.

The dye composition according to the invention may be in various forms, such as in the form of creams or gels, or in any other form suitable for dyeing keratin fibres, and in particular human hair.

The process for dyeing keratin fibres of the present invention is a process in which the composition according to the present invention as defined above is applied to the fibres, preferably in the presence of at least one oxidizing agent for a period of time sufficient to develop the desired colour. The colour may be revealed at acidic, neutral or alkaline pH and the oxidizing agent(s) may be added to the composition of the invention just at the time of use or it (they) may be used starting from an oxidizing composition containing it (them), applied simultaneously with or sequentially to the composition of the invention.

According to a specific embodiment, the composition according to the present invention is a ready-to-use composition which is mixed, preferably at the time of use, with a composition containing, in a medium suitable for dyeing, at least one oxidizing agent, this oxidizing agent (or these oxidizing agents) being present in a sufficient amount to develop a colouration. The mixture obtained is subsequently applied to the keratin fibres. After a leave-on time of approximately 3 to 50 minutes, preferably approximately 5 to 30 minutes, the keratin fibres are rinsed, washed with shampoo, rinsed again, and then dried.

The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases, such as uricases, and 4-electron oxigenases such as laccases, these oxidoreductases being optionally combined with their customary cofactors such as uric acid for uricases. The preferred oxidizing agent is hydrogen peroxide.

The oxidizing composition may also contain various adjuvants normally used in compositions for dyeing the hair, as defined above.

The pH of the oxidizing composition containing the oxidizing agent is such that, after mixing with the dye composition, the pH of the resulting composition applied to the keratin fibres preferably ranges from 3 to 12 approximately, and preferentially from 5 to 10. It may be adjusted to the desired value by means of acidifying or basifying agents normally used in the dyeing of keratin fibres, as defined above.

The ready-to-use composition which is finally applied to the keratin fibres may be in various forms, such as in the form of creams or gels, or in any other form suitable for dyeing keratin fibres, and in particular human keratin fibres such as the hair.

A subject of the invention is also a multicompartment dyeing device or dyeing "kit", comprising at least a first compartment containing the dye composition as defined above and at least a second compartment containing an oxidizing composition. This device may be equipped with a means for delivering the desired mixture to the hair, such as the devices described in Patent Application FR-A-2 586 913.

The examples which follow serve to illustrate the invention without, however, being limiting in nature.

EXAMPLES

The following compositions were prepared.

|  | Composition 1 | Composition 2 |
|---|---|---|
| 1-methyl-2,5-diaminobenzene | 1.7 g | 0.5 g |
| 1-hydroxy-4-aminobenzene | — | 0.4 g |
| 1,3-dihydroxybenzene | 1 g | 0.25 g |
| 1-hydroxy-3-aminobenzene | 0.07 g | — |
| 1-beta-hydroxyethyloxy-2,4-diaminobenzene dihydrochloride | 0.03 g | — |
| 2-methyl-1,3-dihydroxybenzene | 0.5 g | 0.3 g |
| 1-methyl-2-hydroxy-4-aminobenzene | — | 0.25 g |
| 1-methyl-2-hydroxy-4-beta-hydroxyethylaminobenzene | — | 0.05 g |
| 6-hydroxyindole | — | 0.01 g |
| Oxyethylenated sorbitan monolaurate (4 EO) (Tween 21, Uniqema) | 5 g | 5 g |
| Cationic cellulose ether (Softcat SL-100 sold by Amerchol) | 0.3 g | 0.5 g |
| Hydroxypropylmethylcellulose | 0.2 g | — |
| Glycol distearate | — | 2 g |
| $C_{18}$-$C_{22}$ fatty alcohols | 3 g | 3 g |
| Oleyl alcohol | — | 1 g |
| Lauric acid monoethanolamide | 5 g | 2 g |
| Mixture of steareth-2 and steareth-21 | 9 g | 7 g |
| Oleic acid | 3 g | 2.6 g |
| Glycerol | — | 5 g |
| Mixture of (myristyl/cetyl/stearyl) myristate/palmitate/stearate (spermacetiwax sold by Laserson) | — | 5 g |
| Pure monoethanolamine | 5.7 g | 0.61 g |
| Aqueous solution of ammonia at 20% by weight | — | 10 g |
| Aqueous solution at 40% by weight of polyquaternium-6 (Merquat 100 sold by Ondeo) | 4 g | 5 g |
| Aqueous solution at 60% by weight of hexadimethrine chloride (Mexomer PO, Chimex) | 2 g | 0.5 g |
| Reducing agent, antioxidant, sequestrant agent, fragrance | q.s. | q.s. |
| Demineralized water q.s. | 100 g | 100 g |

Application Protocol

Each composition is diluted, extemporaneously, with one and half times its weight of aqueous hydrogen peroxide (pH in the region of 3) at 9 volumes (i.e. 2.7% by weight of $H_2O_2$) for composition 1 and at 20 volumes (i.e. 6% by weight of $H_2O_2$) for composition 2. The mixture thus prepared has a good viscosity and is easily applied to grey hair, containing 90% white hairs, at a rate of 10 g per 1 g of hair, for 20 minutes. The hair is then easily rinsed, washed with a standard shampoo and dried.

The hair colour is evaluated visually. The results obtained on natural grey hair, containing 90% white hairs, after treatment, are the following:

|  | Shade |
|---|---|
| Composition 1 | Natural chestnut |
| Composition 2 | Coppery mahogany dark blonde |

These colourations have good properties, in particular in terms of selectivity and fastness. They also have good strength. The compositions obtained are stable over time.

The following compositions were also prepared:

|  | Composition 3 | Composition 4 |
|---|---|---|
| 1-methyl-2,5-diaminobenzene | 0.77 g | 0.007 g |
| 1-beta-hydroxyethyloxy-2,4-diaminobenzene dihydrochloride | 0.02 g | — |
| 1,3-dihydroxybenzene | 0.66 g | 0.012 g |
| 1-hydroxy-3-aminobenzene | 0.14 g | — |
| 1-hydroxy-4-aminobenzene | — | 0.007 g |
| Oxyethylenated sorbitan monolaurate (4 EO) (Tween 21, Uniqema) | 5 g | 6 g |
| Cationic cellulose ether (Softcat SL-100 sold by Amerchol) | 0.15 g | 0.15 g |
| Xanthan gum | 0.2 g | 0.2 g |
| Oleyl alcohol | 2.7 g | 2.7 g |
| Cetylstearyl alcohol | 16.2 g | 16.2 g |
| Oleth-30 | 3.6 g | 3.6 g |
| Oleic acid | 2.7 g | 2.7 g |
| Aqueous solution at 60% by weight of hexadimethrine chloride (Mexomer PO, Chimex) | 5 | 5 |

|  | Composition 3 | Composition 4 |
|---|---|---|
| Pure monoethanolamine | 0.63 g | 0.63 g |
| Aqueous solution of ammonia at 20% by weight | 11.1 g | 19.8 g |
| Reducing agent, antioxidant, sequestrant agent, fragrance | q.s. | q.s. |
| Demineralized water q.s. | 100 g | 100 g |

Application Protocol

Each composition is diluted, extemporaneously, with one and half times its weight of aqueous hydrogen peroxide (pH in the region of 3) at 20 volumes for composition 3 and with twice its volume of aqueous hydrogen peroxide at 30 volumes (i.e. 9% by weight of $H_2O_2$) for composition 4. The mixture thus prepared has a good viscosity and is easily applied to grey hair, containing 90% white hairs, at a rate of 10 g per 1 g of hair, for 30 minutes for composition 3 and 45 minutes for composition 4. The hair is then easily rinsed, washed with a standard shampoo and dried.

The hair colouration is evaluated visually. The results obtained for the natural grey hair, containing 90% white hairs, after treatment, are the following:

|  | Shade |
|---|---|
| Composition 3 | Natural light chestnut |
| Composition 4 | Naturally very very light blonde |

These colourations have good properties, in particular in terms of selectivity and fastness. The compositions obtained are stable over time.

The invention claimed is:

1. Dye composition for keratin fibers, comprising, in a medium suitable for dyeing:
   A) one or more cationic cellulose ether(s) comprising from 4000 to 10 000 anhydroglucose units, said anhydroglucose units being substituted with at least:
      (i) one substituent of formula $[R_4R_5R_6R_9N^+](X_2^-)$, in which:
         $R_4$ and $R_5$ represent, independently of one another, a methyl or ethyl group,
         $R_6$ represents a linear or branched $C_8$-$C_{24}$ alkyl group or an aralkyl group in which the linear or branched alkyl part is $C_8$-$C_{24}$,
         $R_9$ represents a divalent group which allows the attachment to the anhydroglucose group and which is chosen from $-(B)_q-CH_2-CHOH-CH_2-$ and $-CH_2CH_2-$,
         q denoting 0 or 1,
         B denoting a divalent group $-(CH_2CH_2O)_{n'}-$,
         n' being an integer ranging from 1 to 100,
         $X_2^-$ represents an anion; and
      (ii) one substituent of formula $[R_1R_2R_3R_8N^+](X_1^-)$, in which:
         $R_1$, $R_2$ and $R_3$ represent, independently of one another, a methyl or ethyl group,
         $R_8$ represents a divalent group which allows the attachment to the anhydroglucose group and which is chosen from $-(A)_p-CH_2-CHOH-CH_2-$ and $-CH_2CH_2-$, p denoting 0 or 1,
   A denoting a divalent group $-(CH_2CH_2O)_n-$,
   n being an integer ranging from 1 to 100,
   $X_1^-$ represents an anion;
   B) one or more weakly oxyethylenated sorbitan fatty acid ester(s); and
   C) one or more oxidation dye(s).

2. Dye composition according to claim 1, wherein the cationic cellulose ether is formed from at least one unit (IV) and at least one of the following units (I), (II) or (III):

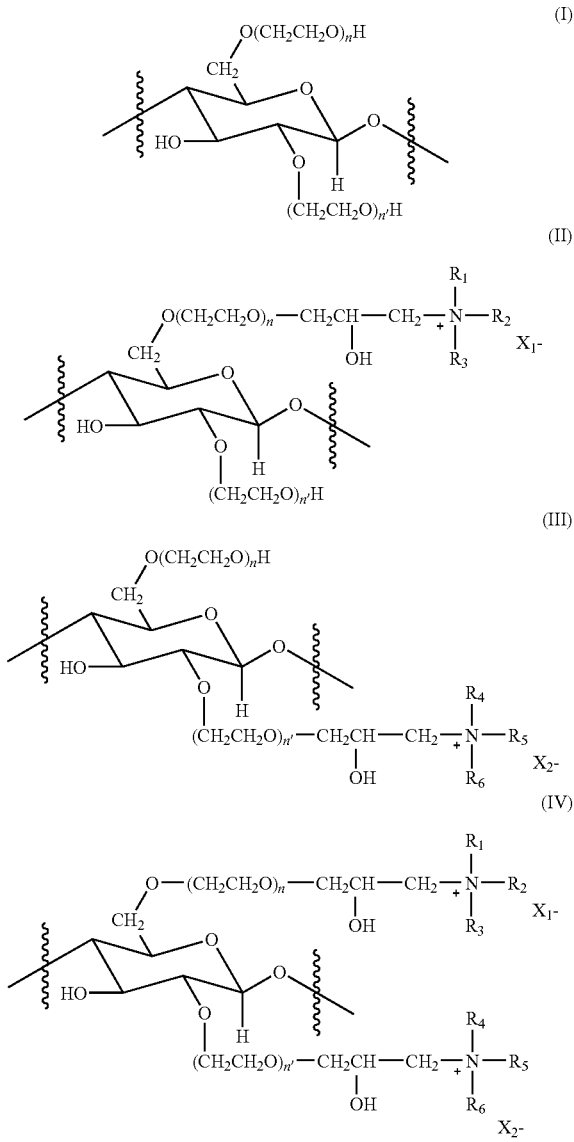

with the proviso that:
   the total number of units (I)+(II)+(III)+(IV) is between 4000 and 10 000;
   the ratio of units [(III)+(IV)]/[(I)+(II)+(III)+(IV)] ranges from 0.0003 to 0.8;
   the ratio of units [(II)+(IV)]/[(I)+(II)+(III)+(IV)] ranges from 0.02 to 0.9;
   the integers n and n', independently of one another, range from 0 to 5;
   $R_1$, $R_2$, $R_3$, $R_4$ and $R_5$ represent, independently of one another, a methyl or ethyl group;

R$_6$ represents a linear or branched C$_8$-C$_{24}$ alkyl group or an aralkyl group in which the linear or branched alkyl part is C$_8$-C$_{24}$;

X$_1^-$ and X$_2^-$ represent anions chosen, independently of one another, from phosphate, nitrate, sulphate and halide ions.

3. Dye composition according to claim 2, wherein R$_6$ represents a linear or branched alkyl group containing from 12 to 15 carbon atoms.

4. Dye composition according to claim 1, wherein the concentration of cationic cellulose ether(s) ranges from 0.01% to 10% by weight.

5. Cosmetic composition according to claim 1, wherein the oxyethylenated sorbitan fatty acid ester comprises fewer than 10 ethylene oxide units.

6. Cosmetic composition according to the claim 5, wherein the oxyethylenated sorbitan fatty acid ester comprises from 2 to 9 ethylene oxide units.

7. Cosmetic composition according to claim 1, wherein the fatty acid of the oxyethylenated sorbitan ester is a linear fatty acid.

8. Cosmetic composition according to claim 1, wherein the fatty acid of the oxyethylenated sorbitan ester is a saturated fatty acid.

9. Cosmetic composition according to claim 1, wherein the concentration of oxyethylenated sorbitan fatty acid ester(s) ranges from 1% to 20% by weight, relative to the total weight of the composition.

10. Dye composition according to claim 1, wherein that the oxidation dye is chosen from benzene, heterocyclic and naphthalene oxidation dyes.

11. Dye composition according to claim 10, wherein the oxidation dye is chosen from cationic or noncationic benzene bases, heterocyclic bases, benzene couplers, heterocyclic couplers and naphthalene couplers.

12. Dye composition according to claim 11, wherein the oxidation dye is a benzene oxidation base chosen from para-phenylenediamines, bisphenylalkylenediamines, para-aminophenols, ortho-aminophenols, and addition salts thereof.

13. Dye composition according to claim 12, wherein the benzene oxidation base is a para-phenylenediamine chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and addition salts thereof.

14. Dye composition according to claim 12, wherein the benzene oxidation base is a bisphenylalkylenediannine chosen from N,N'-bis(β-hydroxyethyl)-N,N'-bis(4'-aminophenyl)-1,3diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis-(4-methylanninophenyl)tetramethylenediarnine, N,N'-bis(ethyl)-N,N'-bis(4'-amino, 3'-methylphenyl)ethylenediamine, 1,8-bis(2,5-diaminophenoxy)-3,6-dioxaoctane, and addition salts thereof.

15. Dye composition according to claim 12, wherein the benzene oxidation base is a para-aminophenol chosen from para-aminophenol, 4-amino-3-methylphenol, 4-amino-3-fluorophenol, 4-amino-3-hydroxymethylphenol, 4-amino-2-methylphenol, 4-amino2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and addition salts thereof.

16. Dye composition according to claim 12, wherein the benzene oxidation base is an ortho-aminophenol chosen from 2-aminophenol, 2-amino-5-methylphenol, 2-amino-6-methylphenol, 5-acetamido-2-aminophenol, and addition salts thereof.

17. Dye composition according to claim 11, wherein the oxidation dye is a benzene oxidation base chosen from cationic para-phenylenediamines, cationic para-aminophenols, cationic ortho-phenylenediamines, cationic ortho-aminophenols or double cationic bases of the family of bis(aminophenyl)alkylenediamines, bearing at least one quaternary nitrogen atom.

18. Dye composition according to claim 17, wherein the cationic benzene oxidation base is a para-phenylenediamine, at least one of the amine functions of which is a tertiary amine, bearing at least one pyrrolidine nucleus, the para-phenylenediamine molecule having at least one quaternized nitrogen atom.

19. Dye composition according to claim 18, wherein the cationic para-phenylenediamine is chosen from the following compounds:

[1-(4-aminophenyl)pyrrolidin-3-yl]trimethylammonium; chloride,

[1-(4-aminophenyl)pyrrolidin-3-yl]dimethyltetradecylammonium; bromide,

3-[1-(4-aminophenyl)pyrrolidin-3-yl]-1-methyl-3H-imidazol-1-ium; chloride,

[1-(4-aminophenyl)pyrrolidin-3-yl]-(2-hydroxyethyl) dimethylammonium; chloride,

[1-(4-aminophenyl)pyrrolidin-3-yl]dimethyl-(3-trimethylsilanylpropyl)ammonium; chloride,

[1-(4-aminophenyl)pyrrolidin-3-yl]-(3-trimethylammoniumhexyl)dimethylammonium; dichloride, {2-[1(4-aminophenyl)pyrrolidin-3-yloxy]ethyl}trimethylammonium; chloride, 1-{2-[1-(4-aminophenyl)pyrrolidin-3-yloxy]ethyl}-1-methylpyrrolidinium; chloride, 3-{3-[1-(4-aminophenyl)pyrrolidin-3-yloxy]propyl}-1-methyl-3H-imidazol-1-ium; chloride, 1-{2-[1-(4-aminophenyl)pyrrolidin-3-yloxy]ethyl}-1-methylpiperidinium; chloride, 3-{3-[1-(5-trimethylsilanylethyl-4-amino-3-trimethylsilany1ethylphenyl)pyrrolidin-3-yloxy]propyl}-1-methyl-3H-imidazol-1-ium; chloride,

[1-(4-amino-3-methylphenyl)pyrrolidin-3-yl]trimethylammonium; chloride,

[1-(4-amino-3-methylphenyl)pyrrolidin-3-yl]dimethyltetradecylammonium; chloride, 3-[1-(4-amino-3-methylphenyl)pyrrolidin-3-yl]-1-methyl-3H-imidazol-1-ium; chloride,
[1-(4-amino-3-methylphenyl)pyrrolidin-3-yl]-(2-hydroxyethyl)dimethylammonium; chloride,
[1-(4-amino-3-methylphenyl)pyrrolidin-3-yl]dimethyl-(3-trimethylsilanylpropylammonium; chloride,
[1-(4-amino-3-methylphenyl)pyrrolidin-3-yl]-(3-trimethylammoniumhexyl)dimethylammonium; dichloride,
{2-[1-(4-amino-3-methylphenyl)pyrrolidin-3-yloxy]ethyl}-trimethylammonium; chloride,
1-{2-[1-(4-amino-3-methylphenyl)pyrrolidin-3-yloxy]ethyl}-1-methylpyrrolidinium; chloride,
3-{3-[1-(4-amino-3-methylphenyl)pyrrolidin-3-yloxy]propyl}-1-methyl-3H-imidazol-1-um; chloride,
1-{2-[1-(4-amino-3-methylphenyl)pyrrolidin-3-yloxy]ethyl}-1-methylpiperidinium; chloride,
[1-(4-amino-3-trimethylsilanylethylphenyl)pyrrolidin-3-yl]-trimethylammonium; chloride,
3[1-(4-amino-3-trimethylsilanylethylphenyl)pyrrolidin-3-yl]-1-methyl-3H-imidazol-1-ium; chloride,
3-{3[1-(4-amino-3-trimethylsilanylethylphenyl)pyrrolidin-3-yl-oxy]propyl}-1-methyl-3H-imidazol-1-ium; chloride,
[1-(5-trimethylsilanylethyl-4-amino-3-trimethylsilanylethylphenyl)pyrrolidin-3-yl]trimethylammonium; chloride,
3-[1-(5-trimethylsilanylethyl-4-amino-3-trimethylsilanylethylphenyl)pyrrolidin-3-yl]-1-methyl-3H-imidazol-1-ium; chloride,
1'-(4-aminophenyl)-1-methyl[1,3']-bipyrrolidinyl-1-ium; chloride,
1'-(4-amino-3-methylphenyl)-1-methyl[1,3']-bipyrrolidinyl-1-ium; chloride,
3-{[1-(4-aminophenyl)pyrrolidin-3-ylcarbamoyl]methyl}-1-methyl-3H-imidazol-1-ium; chloride,
3-{[1-(4-amino-3-methylphenyl)pyrrolidin-3-ylcarbamoyl]methyl}-1-methyl-3H-imidazol-1-ium; chloride,
3[1-(4-aminophenyl)pyrrolidin-3-yl]-1 -(3-trimethylsilanylpropyl)-3H-imidazol-1-ium; chloride,
3[1 -(4-aminophenyl)pyrrolidin-3-yl]-1 -(3-trimethylsilanylpropyl)-3H-imidazol-1-ium; chloride,
[1-(4-aminophenyl)pyrrolidin-3-yl]ethyldimethylammonium; chloride,
[1-(4-aminophenyl)pyrrolidin-3-yl]ethyldimethylammonium; iodide,
[1-(4-aminophenyl)pyrrolidin-3-yl]propyldimethylammonium; iodide,
[1-(4-aminophenyl)pyrrolidin-3-yl]propyldimethylammonium; bromide,
[1-(4-aminophenyl)pyrrolidin-3-yl]propyldimethylammonium; methosulphate,
[1-(4-aminophenyl)pyrrolidin-3-yl]butyldimethylammonium; iodide,
[1-(4-aminophenyl)pyrrolidin-3-yl]pentyldimethylammonium; iodide
[1-(4-aminophenyl)pyrrolidin-3-yl]hexyldimethylammonium; iodide,
[1-(4-aminophenyl)pyrrolidin-3-yl]heptyldimethylammonium; iodide,
[1-(4-aminophenyl)pyrrolidin-3-yl]octyldimethylammonium; iodide,
[1-(4-aminophenyl)pyrrolidin-3-yl]decyldimethylammonium; iodide,
[1-(4-aminophenyl)pyrrolidin-3-yl]hexadecyldimethylammonium; iodide,
[1-(4-aminophenyl)pyrrolidin-3-yl]hydroxyethyldimethylammonium; chloride, and
[1-(4-aminophenyl)pyrrolidin-3-yl]hydroxyethyldimethylammonium; iodide.

20. Dye composition according to claim 11, wherein the oxidation dye is a heterocyclic oxidation base chosen from pyridines, pyrimidines, pyrazoles, condensed pyrazolopyrimidines, pyrazolotriazoles, pyrazolotetrazoles, pyrazolopyridazines, pyrazolothiazoles, pyrazoloimidazoles, pyrazolobenzimidazoles, pyrazoloquinolines, aminopyrolidines, aminopyrazolines, mono- or diaminotetraquinolines, diamino- or triaminoquinolines, aminoindazoles, diaminouracils, aminoindolenines, hydrazones, julolidine or lilolidine, and also derivatives thereof and addition salts thereof.

21. Dye composition according to claim 20, wherein the heterocyclic base is chosen from pyridines, pyrimidines, pyrazoles and pyrazolopyrimidines.

22. Dye composition according to claim 21, wherein the heterocyclic base is chosen from 4,5-diaminopyrazoles.

23. Dye composition according to claim 11, wherein the oxidation dye is a benzene coupler chosen from meta-aminophenols, meta-phenylenediamines, meta-diphenols, and addition salts thereof.

24. Dye composition according to claim 23, wherein the benzene coupler is a meta-aminophenol chosen from the compounds of formula (V) below:

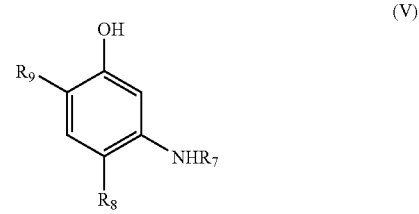

in which:

$R_7$ represents a hydrogen atom, a $C_1$-$C_4$ alkyl group, a $C_1$-$C_4$ monohydroxyalkyl group or a $C_2$-$C_4$ polyhydroxyalkyl group;

$R_8$ represents a hydrogen atom, a $C_1$-$C_4$ alkyl group, a $C_1$-$C_4$ alkoxyl group or a halogen atom chosen from chlorine, bromine or fluorine;

$R_9$ represents a hydrogen atom, a $C_1$-$C_4$ alkyl group, a $C_1$-$C_4$ alkoxyl group, a $C_1$-$C_4$ monohydroxyalkyl group, a $C_2$-$C_4$ polyhydroxyalkyl group, a $C_1$-$C_4$ monohydroxyalkoxyl group or a $C_2$-$C_4$ polyhydroxyalkoxyl group; and from addition salts thereof.

25. Dye composition according to claim 24, wherein the compound of formula (V) is chosen from meta-aminophenol, 5-amino-2-methoxyphenol, 5-amino-2-(betahydroxyethyloxy)phenol, 5-amino-2-methylphenol, 5-N-(β-hydroxyethyl)amino-2-methylphenol, 5-N-(beta-hydroxyethyl)amino-4-methoxy-2-methylphenol, 5-amino-4-methoxy-2-methylphenol, 5amino-4-chloro-2-methylphenol, 5-amino-2,4-dimethoxyphenol, 5-(gamma-hydroxypropylamino)-2-methylphenol, and addition salts thereof.

26. Dye composition according to claim 23, wherein the benzene coupler is a meta-phenylenediamine chosen from the compounds of formula (VI) below:

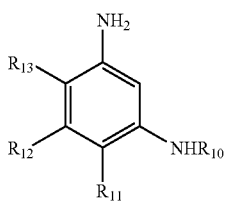

(VI)

in which:
R$_{10}$ represents a hydrogen atom, a C$_1$-C$_4$ alkyl group, a C$_1$-C$_4$ monohydroxyalkyl group or a C$_2$-C$_4$ polyhydroxyalkyl group;
R$_{11}$ and R$^{12}$, which may be identical or different, represent a hydrogen atom, a C$_1$-C$_4$ alkyl group, a C$_1$-C$_4$ monohydroxyalkoxyl group or a C$_2$-C$_4$ polyhydroxyalkoxyl group;
R$_{13}$ represents a hydrogen atom, a C$_1$-C$_4$ alkoxyl group, a C$_1$-C$_4$ aminoalkoxyl group, a C$_1$-C$_4$ monohydroxyalkoxyl group, a C$_2$-C$_4$ polyhydroxyalkoxyl group or a 2,4-diaminophenoxyalkoxyl group; and from addition salts thereof.

27. Dye composition according to claim 26, wherein the compound of formula (VI) is chosen from 2,4diaminobenzene, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(beta-aminoethyloxy)-2,4-diaminobenzene, 2-amino-1-(beta-hydroxyethyloxy)-4-methylaminobenzene, 2,4-diamino-1-ethoxy-5-methylbenzene, 2,4-diamino-5-(beta-hydroxyethyloxy)-1-methylbenzene, 2,4-diamino-1-(beta,gamma-dihydroxypropyloxy)benzene, 2,4-diamino-1-(beta-hydroxyethyloxy)benzene, 2-amino-4-N-(beta-hydroxyethyl)amino-1-methooxybenzene, and addition salts thereof.

28. Dye composition according to claim 23, wherein the benzene coupler is a meta-diphenol chosen from the compounds of formula (VII) below:

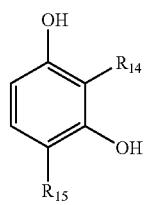

(VII)

in which:
R$_{14}$ and R$_{15}$, which may be identical or different, represent a hydrogen atom, a C$_1$-C$_4$ alkyl group or a halogen atom chosen from chlorine, bromine or fluorine; and from addition salts thereof.

29. Dye composition according to claim 28, wherein the compound of formula (VII) is chosen from 1,3-dihydroxybenzene, 2-methyl-1,3-dihydroxybenzene, 4-chloro-1,3dihydroxybenzene, 2-chloro-1,3-dihydroxybenzene, and addition salts thereof.

30. Dye composition according to claim 11, wherein the oxidation dye is a heterocyclic coupler chosen from azole-containing heterocyclic couplers, pyridine couplers, thiophenes, indolines, indoles, benzofurans, 8-amino-6-methoxyquinolines, 4-hydroxyquinolones, benzodioxoles, hydroxybenzamides, sesamol and its derivatives, benzomorpholines, and also addition salts thereof.

31. Dye composition according to claim 30, wherein the heterocyclic coupler is an indole chosen from 6-hydroxyindole, 5,6-hydroxyindole, 4-hydroxyindole, derivatives thereof, and addition salts thereof.

32. Dye composition according to claim 30, wherein the heterocyclic coupler is a benzomorpholine chosen from 6-hydroxybenzomorpholine, 6-aminobenzomorpholine, and addition salts thereof.

33. Dye composition according to claim 11, wherein the oxidation dye is a naphthalene coupler chosen from alpha-naphthol, substituted naphthalenes of formula (VIII) below, and addition salts thereof:

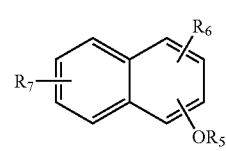

(VIII)

in which:
R$_5$ represents a hydrogen atom or a —CO—R group In which R represents a C$_1$-C$_4$ alkyl group;
R$_6$ represents a hydrogen atom, a hydroxyl group, a C$_1$-C$_4$ alkyl group or an —SO$_3$H group;
R$_7$ represents a hydrogen atom or a hydroxyl group;
it being understood that at least one of groups R$_5$ to R$_7$ is other than a hydrogen atom.

34. Dye composition according to claim 33, wherein the naphthalene coupler is chosen from:
-alpha-naphthol,
-1,7-dihydroxynaphthalene,
-2,7-dihydroxynaphthalene,
-2,5-dihydroxynaphthalene,
-2,3-dihydroxynaphthalene,
-1-acetoxy-2-methylnaphthalene,
-1-hydroxy-2-methylnaphthalene,
-1-hydroxy-4-naphthalenesulphonic acid, and addition salts thereof.

35. Dye composition according to claim 1, wherein the concentration of oxidation dye(s) ranges from 0.005% to 15% by weight, relative to the total weight of the composition.

36. Dye composition according to claim 1, further comprising one or more direct dye(s) chosen from nitrobenzene dyes, azo direct dyes, methine direct dyes, and addition salts thereof.

37. Dye composition according to claims 1, further comprising one or more adjuvant(s) chosen from additional anionic, cationic, nonionic, amphoteric or zwitterionic surfactants -other than the sorbitan fatty acid esters defined in one of claims 5 to 8, or mixtures thereof; additional nonionic, amphoteric, zwitterionic, anionic or cationic polymers -other than the cationic cellulose ethers defined in one of claims 1 to 3, or mixtures thereof; antioxidants; penetrating agents; sequestrant agents; fragrances; buffers; dispersants; conditioning agents; film-forming agents; ceramides; preservatives; opacifiers; vitamins; amino acids; oligopeptides; peptides; modified or unmodified, hydrolysed or nonhydrolysed proteins; enzymes; branched or unbranched fatty acids and fatty alcohols; animal, plant or mineral waxes; hydroxylated organic acids; UV screens; antioxidants and free-radical scavengers; anti-dandruff agents; agents for regulating seborrhoea; calmatives; mineral, plant or animal oils; polyisobutenes and poly(alpha-olefins); pigments; acids, bases, plasticizers, mineral fillers, pearlescent agents, flakes; antistatic agents and reducing agents.

38. Cosmetic composition according to claim 1, further comprising at least one thickener.

39. Dye composition according to claim 1, wherein the pH of the composition ranges from 3 to 12.

40. Dye composition according to one of claim 1, further comprising at least one oxidizing agent chosen from hydrogen peroxide, urea peroxide, alkali metal bromates, persalts, peracids and oxidase enzymes.

41. Process for oxidation dyeing keratin fibers, wherein a dye composition as defined in claim 1 is applied to the fibers in the presence of at least one oxidizing agent for a period of time sufficient to develop the desired colour.

42. Multicompartment device, comprising at least a first compartment containing a dye composition as defined in claim 1 and at least a second compartment containing at least one oxidizing agent.

43. Use of the composition defined in claim 1 for dyeing keratin fibers.

* * * * *

UNITED STATES PATENT AND TRADEMARK OFFICE
CERTIFICATE OF CORRECTION

| | | |
|---|---|---|
| PATENT NO. | : 8,002,847 B2 | |
| APPLICATION NO. | : 12/671448 | |
| DATED | : August 23, 2011 | |
| INVENTOR(S) | : Marie-Pascale Audousset et al. | |

It is certified that error appears in the above-identified patent and that said Letters Patent is hereby corrected as shown below:

Claim 14, col. 38, line 2, "1,3diaminopropanol" should read
-- 1,3-diaminopropanol --.

Claim 15, Col. 38, line 16, "4-amino2-hydroxymethylphenol" should read
-- 4-amino-2-hydroxymethylphenol --.

Claim 25, col. 40, line 62, "5amino" should read -- 5-amino --.

Claim 33, col. 42, line 26, "In which" should read -- in which --.

Signed and Sealed this
First Day of November, 2011

David J. Kappos
*Director of the United States Patent and Trademark Office*